United States Patent
Truong et al.

(10) Patent No.: US 10,500,297 B2
(45) Date of Patent: Dec. 10, 2019

(54) APPARATUS AND METHOD FOR DETECTING IMPROPER POSITIONING OF REMOVABLE COMPONENT OF STERILIZING SYSTEM

(71) Applicant: ASP Global Manufacturing GmbH, Schaffhausen (CH)

(72) Inventors: Doug Vo Truong, Irvine, CA (US); Lawrence Y. Mok, Hacienda Heights, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 211 days.

(21) Appl. No.: 15/356,724

(22) Filed: Nov. 21, 2016

(65) Prior Publication Data
US 2018/0140731 A1    May 24, 2018

(51) Int. Cl.
*A61L 2/00* (2006.01)
*B08B 3/00* (2006.01)
(Continued)

(52) U.S. Cl.
CPC .............. *A61L 2/24* (2013.01); *A61L 2/18* (2013.01); *A61L 2/20* (2013.01); *A61L 2/208* (2013.01);
(Continued)

(58) Field of Classification Search
CPC ........ A61L 2/00; A61L 2/0088; A61M 5/001; A61B 1/00; A61B 1/121; A61B 1/123
USPC ..... 600/101, 133; 134/43, 56 R, 109, 166 R; 239/309; 422/292, 300; 221/30, 154, 221/197; 222/80
See application file for complete search history.

(56) References Cited

U.S. PATENT DOCUMENTS 4,913,196 A * 4/1990 Williams .................. A61L 2/24
141/1
5,219,099 A * 6/1993 Spence ............... A61M 5/1456
222/325
(Continued)

FOREIGN PATENT DOCUMENTS

| EP | 1 121 942 A2 | 8/2001 |
| EP | 1 570 864 A2 | 9/2005 |
| EP | 1 600 174 A2 | 11/2005 |

OTHER PUBLICATIONS

U.S. Appl. No. 62/316,722, filed Apr. 1, 2016.
European Search Report, Partial, and Provisional Written Opinion dated May 22, 2018 for Application No. EP 17202523.1, 17 pgs.
European Search Report and Written Opinion dated Aug. 27, 2018 for Application No. EP 17202523.1, 16 pgs.

*Primary Examiner* — Monzer R Chorbaji
(74) *Attorney, Agent, or Firm* — Frost Brown Todd LLC

(57) ABSTRACT

A sterilization system includes a sterilization chamber, a processor, and a sterilization module. The sterilization module includes a frame assembly, an extraction assembly, and a carriage assembly. The extraction assembly is configured to extract a sterilant fluid from a cartridge and transfer the sterilant fluid to the sterilization chamber. The carriage assembly includes a motor, a carriage body, and a translating flag. The carriage body is configured to receive the cartridge. The translating flag is configured to move from a first position to a second position relative to the carriage body in response to the carriage body receiving the cartridge. The sensor is configured to detect movement of the translating flag from the first position to the second position.

20 Claims, 28 Drawing Sheets

(51) Int. Cl.
    *A62C 13/62*     (2006.01)
    *G07F 11/72*     (2006.01)
    *A47F 1/04*     (2006.01)
    *A61L 2/24*     (2006.01)
    *A61L 2/20*     (2006.01)
    *A61L 2/18*     (2006.01)
    *A61L 2/28*     (2006.01)
    *A61L 2/04*     (2006.01)
    *A61L 2/14*     (2006.01)

(52) U.S. Cl.
    CPC . *A61L 2/28* (2013.01); *A61L 2/04* (2013.01); *A61L 2/14* (2013.01); *A61L 2202/121* (2013.01); *A61L 2202/14* (2013.01); *A61L 2202/15* (2013.01); *A61L 2202/24* (2013.01)

(56) References Cited

U.S. PATENT DOCUMENTS

| | | |
|---|---|---|
| 6,325,972 B1 | 12/2001 | Jacobs et al. |
| 6,365,102 B1 | 4/2002 | Wu et al. |
| 6,447,719 B1 | 9/2002 | Agamohamadi et al. |
| 6,852,277 B2 | 2/2005 | Platt et al. |
| 6,852,279 B2 | 2/2005 | Williams et al. |
| 6,939,519 B2 | 9/2005 | Agamohamadi et al. |
| 8,440,139 B2 | 5/2013 | Choperena et al. |
| 2006/0173480 A1* | 8/2006 | Zhang ................ A61B 17/3494 606/185 |

\* cited by examiner

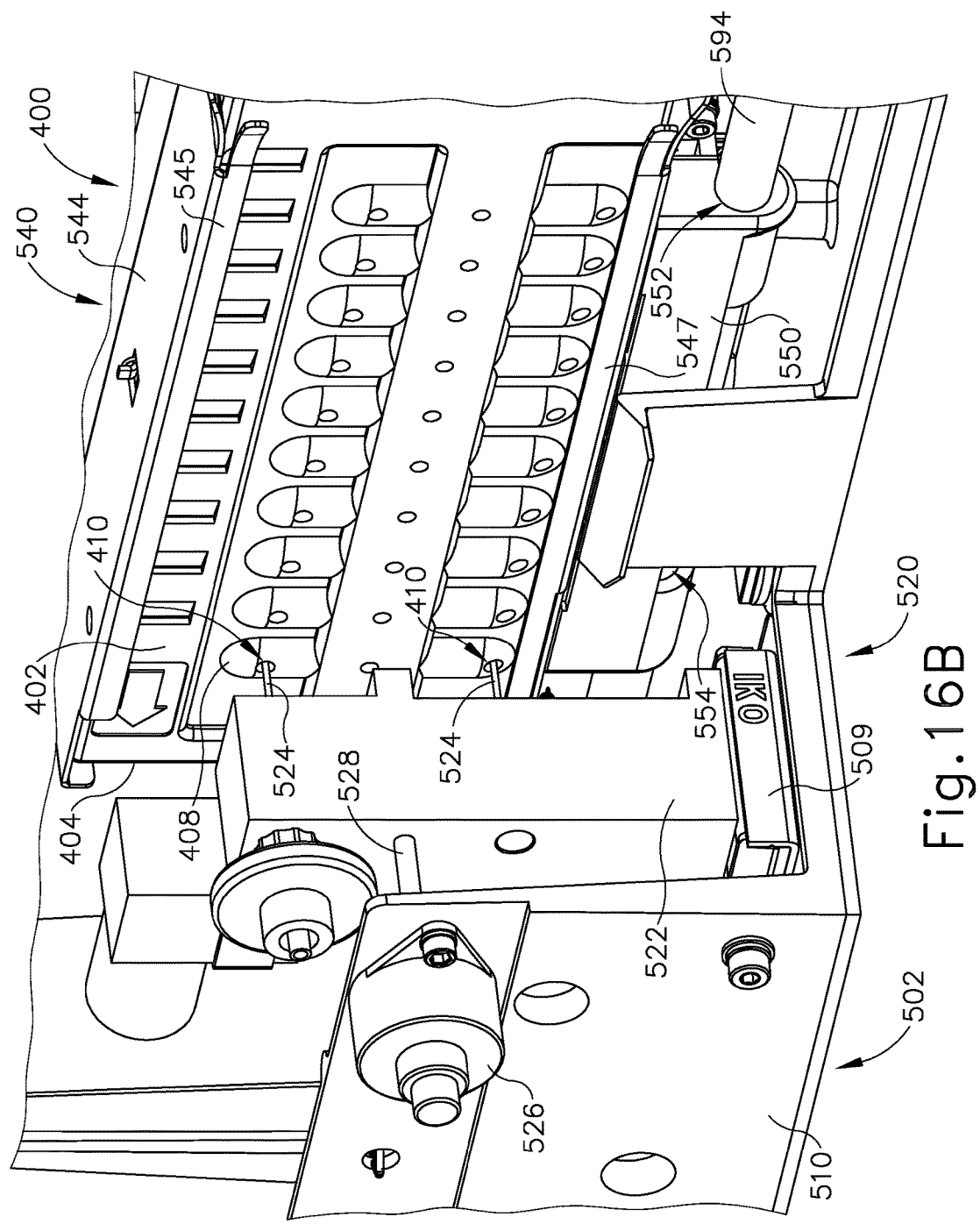

# APPARATUS AND METHOD FOR DETECTING IMPROPER POSITIONING OF REMOVABLE COMPONENT OF STERILIZING SYSTEM

BACKGROUND

Re-usable medical devices such as certain surgical instruments, endoscopes, etc., may be sterilized before re-use in order to minimize the likelihood that a contaminated device might be used on a patient, which could cause an infection in the patient. Various sterilization techniques may be employed, such as steam, hydrogen peroxide, peracetic acid, and vapor phase sterilization, either with or without a gas plasma and ethylene oxide (EtO). Each of these methods may depend to a certain extent on the diffusion rates of the sterilization fluids (e.g., gases) upon or into the medical devices to be sterilized.

Before sterilization, medical devices may be packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device. Diffusion of the sterilant may be particularly problematic for medical devices that have diffusion-restricted spaces therein because these diffusion-restricted spaces may reduce the likelihood that a sterilization cycle may be effective. For example, some endoscopes have one or more long narrow lumens into which the sterilant must diffuse in sufficient concentration for sufficient time to achieve a successful sterilization cycle.

Sterilization of medical devices may be performed with an automated sterilization system such as a STERRAD® System by Advanced Sterilization Products of Irvine, Calif. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein; U.S. Pat. No. 6,852,279, entitled "Sterilization with Temperature-Controlled Diffusion Path," issued Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; U.S. Pat. No. 6,447,719, entitled "Power System for Sterilization Systems Employing Low Frequency Plasma," issued Sep. 10, 2002, the disclosure of which is incorporated by reference herein; and U.S. Provisional Pat. App. No. 62/316,722, entitled "System and Method for Sterilizing Medical Devices," filed Apr. 1, 2016, the disclosure of which is incorporated by reference herein.

Some sterilization systems may use vaporized chemical sterilants or chemical gas such as hydrogen peroxide, peracetic acid, ozone, chlorine dioxide, nitrogen dioxide, etc., to sterilize medical devices. Examples of such systems are described in U.S. Pat. No. 6,365,102, entitled "Method of Enhanced Sterilization with Improved Material Compatibility," issued Apr. 2, 2002, the disclosure of which is incorporated by reference herein, and U.S. Pat. No. 6,325,972, entitled "Apparatus and Process for Concentrating a Liquid Sterilant and Sterilizing Articles Therewith," issued Dec. 4, 2001, the disclosure of which is incorporated by reference herein. Some such systems provide a hydrogen peroxide/gas plasma sterilization system comprising a vacuum chamber and plasma source and increased concentration of hydrogen peroxide for sterilization. Some such systems may have difficulty sterilizing lumens of some medical devices if their length exceeds a certain value; or the processing time of such systems may still not be fast enough for some applications. Thus, some medical devices such as long and/or narrow flexible endoscopes may not be completely sterilized by these systems due to the insufficient reach of sterilant vapor to the inside of the channels. Such medical devices might therefore only be disinfected without being sterilized. Sterilization systems that use ethylene oxide may have a relatively long processing time (e.g., longer than 24 hours), which may be undesirable in some cases.

Operator error may result in medical devices that are erroneously believed to be decontaminated being returned to service. Confirming that a sterilization cycle has been efficacious may help medical personnel avoid using a contaminated medical device on a patient. The sterilized medical device might not itself be checked for contaminating organisms because such an activity may introduce other contaminating organisms to the medical device, thereby re-contaminating it. Thus, an indirect check may be performed using a sterilization indicator. A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms may be placed into a sterilization chamber alongside a medical device and subject to a sterilization cycle. After the cycle is complete, the microorganisms in the biological indicator may be cultured to determine whether any of the microorganisms survived the cycle. The presence or absence of living microorganisms in the biological indicator will indicate whether the sterilization cycle was effective.

While a variety of systems and methods have been made and used for surgical instrument sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 16B depicts a perspective view of the sterilant extraction assembly of FIG. 16A actuated toward the cartridge of FIG. 4 in order to extract sterilant from the cartridge;

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Sterilization System

Figure 1:
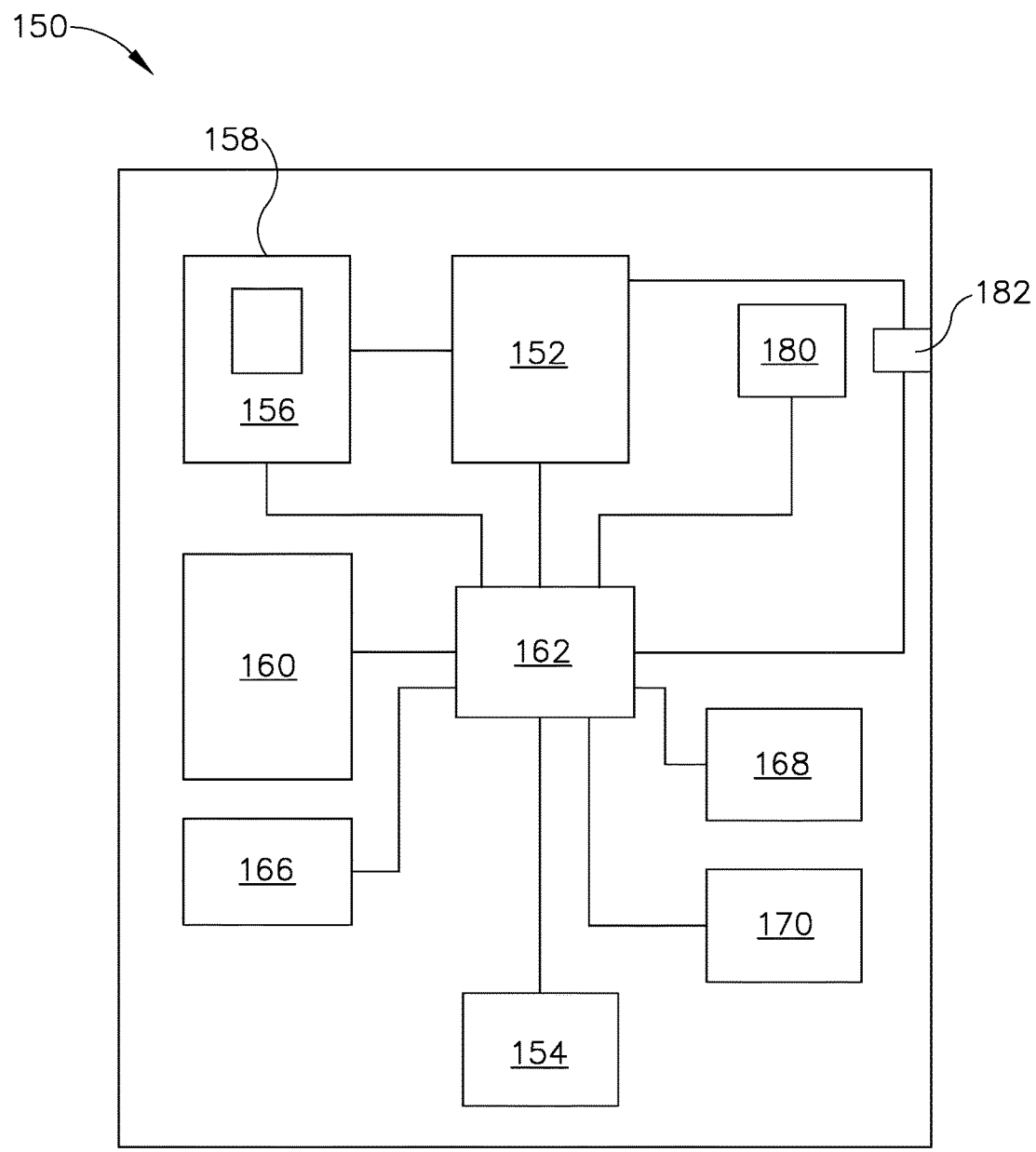
FIG. 1 depicts a schematic view of an exemplary medical device sterilizing cabinet.

FIG. 1 depicts an exemplary sterilizing cabinet (150) that is operable to sterilize medical devices such as endoscopes, etc. Sterilizing cabinet (150) of the present example includes a sterilization chamber (152), which is configured to receive one or more medical devices for sterilization. In some other versions (e.g., as described further below), sterilizing cabinet (150) may include more than one sterilization chamber (152). While not shown, sterilizing cabinet (150) also includes a door that opens and closes sterilization chamber (152) in response to actuation of a kick plate. An operator may thereby open and close sterilization chamber (152) in a hands-free fashion. Of course, any other suitable features may be used to provide selective access to sterilization chamber. Sterilizing cabinet (150) also includes a sterilization module (156) that is operable to dispense a sterilant into sterilization chamber (152) in order to sterilize medical devices contained in sterilization chamber (152). In the present example, sterilization module (156) is configured to receive replaceable sterilant cartridges (158) containing a certain amount of sterilant. By way of example only, each sterilant cartridge (158) may contain enough sterilant to perform five sterilization procedures.

In the present example, sterilization module (156) is operable to apply a sterilant in the form of a vapor within sterilization chamber (152). By way of example only, sterilization module (156) may comprise a combination of a vaporizer and a condenser. The vaporizer may include a chamber that receives a particular concentration of sterilant solution (e.g., a liquid hydrogen peroxide solution with a concentration of about 59% nominal, or between about 53% and about 59.6%); where the sterilant solution changes phase from liquid to vapor. The condenser may provide condensation of the sterilant solution vapor, and the concentration of the sterilant solution may be thereby increased (e.g., from about 59% nominal to somewhere between about 83% nominal and about 95% nominal), by removal of water vapor. Alternatively, any other suitable methods and components may be used to apply sterilant in the form of a vapor within sterilization chamber (152). It should also be understood that condensation within sterilization chamber (152) may serve as a potential reservoir of sterilant that could be tapped by manipulation of conditions in a sterilization chamber (152) to re-vaporize the condensation.

In some examples, to supplement the application of the sterilant in the form of a vapor, the sterilant may also be applied to the inside of lumen(s) and/or other internal spaces within the medical device and/or the outside of the medical device, before the medical device is placed in sterilization chamber (152). By way of example only, sterilant may be applied in liquid form to the inside of lumen(s) and/or other internal spaces within the medical device and/or the outside of the medical device. As another merely illustrative example, a capsule that contains liquid sterilant may be placed in fluid communication with the lumen(s) after activation of sterilization cabinet (150). In versions where a sterilant is applied to the inside of lumen(s) and/or other internal spaces within the medical device and/or the outside of the medical device, before the medical device is placed in sterilization chamber (152), the sterilant may evaporate while a vacuum is applied to sterilization chamber (152) (e.g., as described in greater detail below with reference to block 310 of FIG. 3) and even after vacuum is applied; and provide more concentration of sterilant to the areas of the medical device with less penetration range, thereby further promoting effective sterilization.

Sterilizing cabinet (150) of the present example further includes a touch screen display (160). Touch screen display (160) is operable to render the various user interface display screens, such as those described in U.S. Provisional Pat. App. No. 62/316,722, the disclosure of which is incorporated by reference herein. Of course, touch screen display (160) may display various other screens as well. Touch screen display (160) is further configured to receive user input in the form of the user contacting touch screen display (160) in accordance with conventional touch screen technology. In addition, or in the alternative, sterilizing cabinet (150) may include various other kinds of user input features, including but not limited to buttons, keypads, keyboards, a mouse, a trackball, etc.

Sterilizing cabinet (150) of the present example further includes a processor (162), which is in communication with sterilization module (156) and with touch screen display (160). Processor (162) is operable to execute control algorithms to drive sterilization module (156) in accordance with user input. Processor (162) is further operable to execute instructions to display the various screens on touch screen display (160); and to process instructions received from a user via touch screen display (160) (and/or via other user input features). Processor (162) is also in communication with various other components of sterilization cabinet (150) and is thereby operable to drive those components and/or process input and/or other data from those components. Various suitable components and configurations that may be used to form processor (162) will be apparent to those of ordinary skill in the art in view of the teachings herein.

Sterilizing cabinet (150) of the present example further includes an identification tag reader (166), which is operable to read an identification tag of a biological indicator as described herein. By way of example only, identification tag reader (166) may comprise an optical reader that is operable to read an optical identification tag (e.g., barcode, QR code, etc.) of a biological indicator. In addition, or in the alternative, identification tag reader (166) may comprise RFID reader that is operable to read an RFID identification tag of a biological indicator. Various suitable components and configurations that may be used to form identification tag reader (166) will be apparent to those of ordinary skill in the art in view of the teachings herein. Data received through identification tag reader (166) is processed through processor (162). Such data may indicate the contents of the biological indicator, the source of the biological indicator, other identifying information associated with the biological indicator, and/or various other kinds of information as will be apparent to those of ordinary skill in the art.

Sterilizing cabinet (150) of the present example further includes a memory (168), which is operable to store control logic and instructions and that are executed by processor (162) to drive components such as sterilization module (156), touch screen display (160), communication module (154), and identification tag reader (166). Memory (168) may also be used to store results associated with setup of a sterilization cycle, performance of a load conditioning cycle, performance of a sterilization cycle, and/or various other kinds of information. Various suitable forms that memory (168) may take, as well as various ways in which memory (168) may be used, will be apparent to those of ordinary skill in the art in view of the teachings herein.

Sterilizing cabinet (150) of the present example further includes a printer (170), which is operable to print information such as results associated with setup of a sterilization cycle, performance of a load conditioning cycle, performance of a sterilization cycle, and/or various other kinds of information. By way of example only, printer (170) may comprise a thermal printer, though of course any other suitable kind of printer may be used. Various suitable forms that printer (170) may take, as well as various ways in which printer (170) may be used, will be apparent to those of ordinary skill in the art in view of the teachings herein. It should also be understood that printer (170) is merely optional and may be omitted in some versions.

Sterilizing cabinet (150) of the present example further includes a vacuum source (180) and a venting valve (182). Vacuum source (180) is in fluid communication with sterilization chamber (152) and is also in communication with processor (162). Thus, processor (162) is operable to selectively activate vacuum source (180) in accordance with one or more control algorithms. When vacuum source (180) is activated, vacuum source (180) is operable to reduce the pressure within sterilization chamber (152) as will be described in greater detail below. Venting valve (182) is also in fluid communication with sterilization chamber (152). In addition, venting valve (182) is in communication with processor (162) such that processor (162) is operable to selectively activate venting valve (182) in accordance with one or more control algorithms. When venting valve (182) is activated, venting valve (182) is operable to vent sterilization chamber (152) to atmosphere as will be described in greater detail below. Various suitable components that may be used to provide vacuum source (180) and venting valve (182) will be apparent to those of ordinary skill in the art in view of the teachings herein.

In addition to the foregoing, sterilizing cabinet (150) may be configured and operable in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein.

II. Overview of Exemplary Sterilization Process

Figure 2:
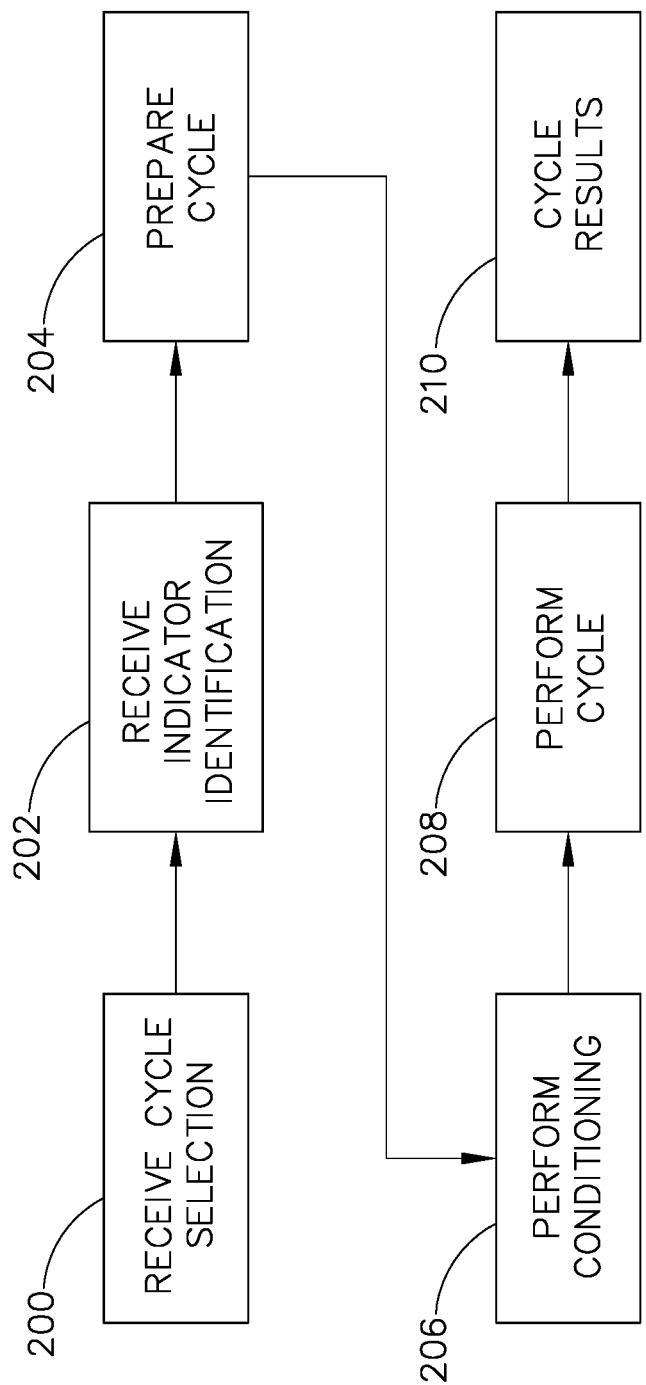
FIG. 2 depicts a high level flowchart of an exemplary set of steps that the sterilizing cabinet of FIG. 1 could perform to sterilize a medical device.

FIG. 2 depicts a high level flowchart of an exemplary set of steps that sterilizing cabinet (150) could perform to sterilize a used medical device, such as an endoscope. Sterilizing cabinet (150) may be configured to perform one or more sterilization cycles, with different sterilization cycles being appropriate for different types and quantities of medical devices. Thus, as an initial step, sterilizing cabinet (150) may display one or more available sterilization cycles via touch screen display (160) and then receive a sterilization cycle selection (block 200) from the user.

Sterilizing cabinet (150) may also display instructions indicating whether a biological indicator should be used with the selected sterilization cycle, and receive a biological indicator identification (block 202). Such a biological indicator identification (block 202) may be provided via identification tag reader (166), via touch screen display (160), or otherwise. A biological indicator may be placed inside sterilization chamber (152) of sterilizing cabinet (150) before the sterilization cycle begins and may remain in sterilization chamber (152) during the sterilization cycle. The user may thus identify the particular biological indicator (block 202) before the biological indicator is placed in sterilization chamber (152). In versions where more than one sterilization chamber (152) is included in a sterilizing cabinet (150), separate biological indicators may be placed in separate sterilization chambers (152). Each biological indicator may contain microorganisms that are responsive to a particular sterilization cycle. Upon completion of the sterilization cycle, the biological indicator may be tested for the microorganisms in order to provide a measure of the effectiveness of the sterilization cycle. A biological indicator may not necessarily be required for all sterilization cycles, but may be required based on hospital rules or local regulations.

Selection of a sterilization cycle (block 200) and identification of a biological indicator (block 202) may define one or more requirements for the configuration and arrangement of medical devices within sterilization chamber (152). Thus, in order to provide preparation for the sterilization cycle (204) once the sterilization cycle has been selected (block 200) and the biological indicator has been identified (block 202), sterilizing cabinet (150) may provide a display via touch screen display (160) indicating a proper medical device placement. This display may serve as a visual guide to a user's placement of medical device(s) (and perhaps a biological indicator) within sterilization chamber (152) of sterilizing cabinet (150), based on the sterilization cycle selection (block 200). A door of sterilization chamber (152) may be opened to enable the user to place the medical device(s) (and perhaps a biological indicator) within sterilization chamber (152) as instructed.

Once the user has placed the medical device in sterilization chamber (152) based on these instructions, the user may press a start button or other button indicating that medical device placement is complete. In some versions, sterilizing cabinet (150) is configured to automatically verify proper medical device placement. By way of example only, sterilizing cabinet (150) may employ photo sensors, imaging devices, weight sensors, and/or other components to verify proper medical device placement in sterilization chamber (152). It should be understood, however, that some versions of sterilizing cabinet (150) may lack the capability of automatically verifying proper placement of a medical device within sterilization chamber (152).

If medical device placement is verified and/or the user has otherwise completed the cycle preparation (block 204), sterilizing cabinet (150) may start a load conditioning process (block 206). Load conditioning process (block 206) prepares sterilization chamber (152) and the medical device(s) within sterilization chamber (152) for optimal sterilization during a sterilization cycle. Conditioning may include controlling and optimizing one or more characteristics of sterilization chamber (152). For example, during load conditioning, sterilizing cabinet (150) may continuously monitor the level of moisture within sterilization chamber (152) while reducing the level of moisture by, for example, circulating and dehumidifying the air of sterilization chamber (152), creating a vacuum within sterilization chamber (152), heating sterilization chamber (152), and/or other methods for dehumidifying a sealed chamber. This may continue until sterilizing cabinet (150) determines that an acceptable level of moisture has been reached.

As part of load conditioning cycle (block 206), sterilizing cabinet (150) may also continuously detect the temperature within sterilization chamber (152) while heating sterilization chamber (152) by, for example, convection of heated air, conduction through an interior surface of sterilization chamber (152), and/or using other techniques. This may continue until sterilizing cabinet (150) determines that an acceptable internal temperature has been reached. Various conditioning actions such as controlling temperature or humidity may be performed in parallel or in sequence. It should also be understood that load conditioning cycle (block 206) may verify that sterilization chamber (152) is sealed; verifying contents of sterilization chamber (152); checking physical characteristics of the contents of sterilization chamber (152) such as content volume, content weight, or other characteristics; and/or performing one or more conditioning steps that may include chemical treatment, plasma treatment, or other types of treatment to reduce moisture, raise temperature, and/or otherwise prepare the medical devices in sterilization chamber (152) for sterilization cycle (block 208).

While the one or more conditioning actions are being performed as part of load conditioning cycle (block 206), sterilizing cabinet (150) may display information via touch screen display (160) indicating to a user the duration of time before sterilization cycle (block 208) performance may begin. Once all load conditioning criteria have been successfully met, load conditioning cycle (block 206) is complete, and sterilization cycle (block 208) may then be performed. It should therefore be understood that sterilizing cabinet (150) is configured such that sterilization cycle (block 208) is not actually initiated until after load conditioning cycle (block 206) is complete. It should also be understood that load conditioning cycle (block 206) may be omitted or varied in some versions of sterilizing cabinet (150) operation.

As noted above, sterilization cabinet (150) may begin performing the sterilization cycle (block 208) automatically and immediately after load conditioning (block 206) has been completed. Sterilization cycle (block 208) may include exposing the medical device(s) in the sterilizing chamber to pressurized sterilant gas, further heat treatment, chemical treatment, plasma treatment, vacuum treatment, and/or other types of sterilization procedures. During performance of sterilization cycle (block 208), sterilization cabinet (150) may display information via touch screen display (160) such as a duration remaining for sterilization cycle (block 208), the current stage of sterilization cycle (block 208) (e.g. plasma, vacuum, injection, heat, chemical treatment), and/or other information.

Figure 3:
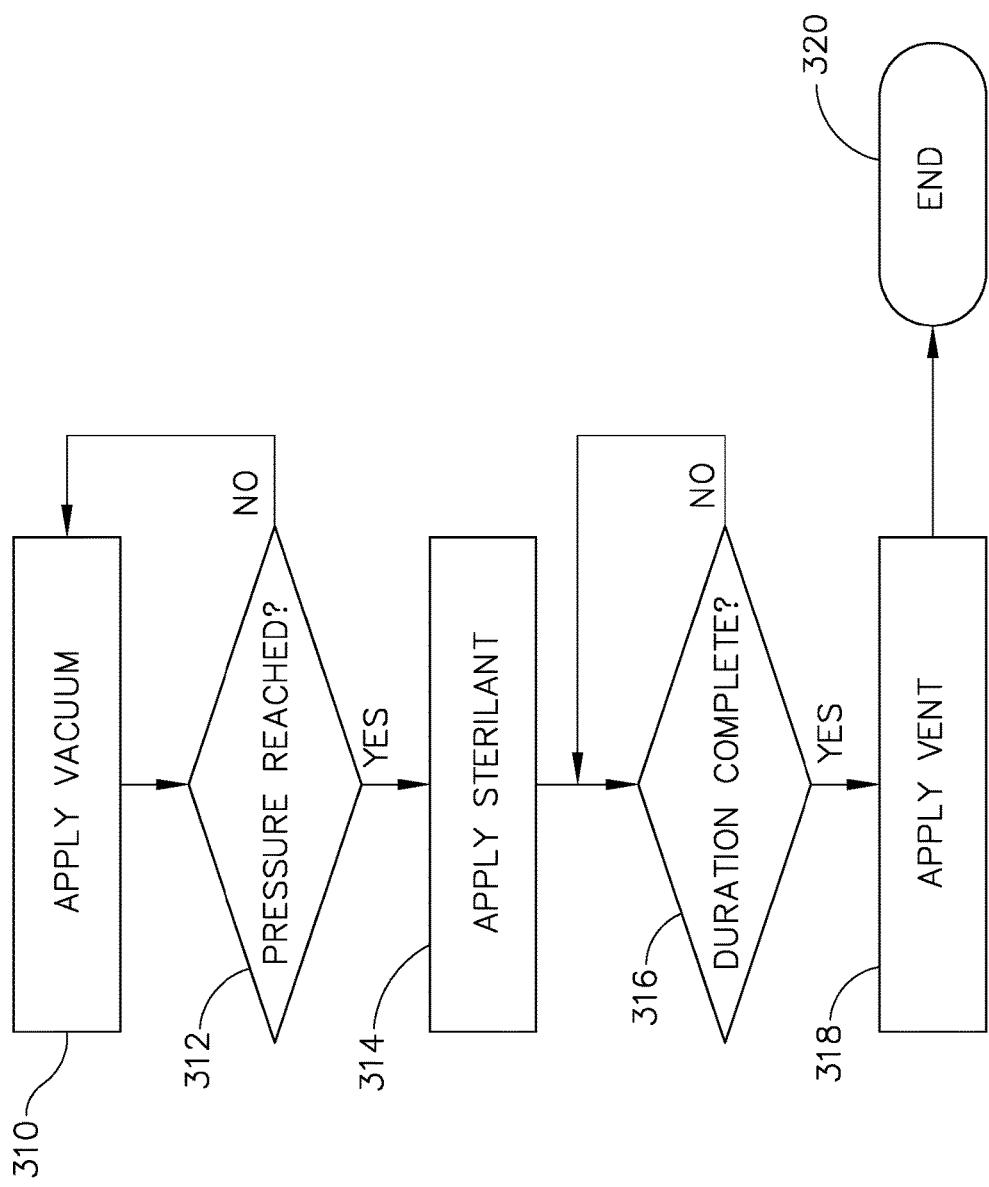
FIG. 3 depicts a flowchart of an exemplary set of steps that may be carried out as part of a sterilization cycle within the set of steps of FIG. 2.

In some versions, sterilization cycle (block 208) includes the exemplary sub-steps shown in FIG. 3. In the example shown in FIG. 3, the cycle begins with a vacuum being applied (block 310) within sterilization chamber (152). In order to provide such a vacuum, processor (162) may activate vacuum source (180) in accordance with a control algorithm. Processor (162) will then determine (block 312) whether a sufficient vacuum pressure level has been reached within sterilization chamber (152). By way of example only, processor (162) may monitor data from one or more pressure sensors within sterilization chamber (152) as part of determination step (block 312). Alternatively, processor (162) may simply activate vacuum source (180) for a predetermined time period and assume that the appropriate pressure has been reached in sterilization (152) based upon the duration for which vacuum source (180) is activated. Other suitable ways in which processor (162) may determine (block 312) whether a sufficient pressure level has been reached within sterilization chamber (152) will be apparent to those of ordinary skill in the art in view of the teachings herein. Until the appropriate pressure level has been reached within sterilization chamber (152), vacuum source (180) will remain activated.

Once sterilization chamber (152) reaches an appropriate pressure level (e.g., between about 0.2 torr and about 10 torr), processor (162) then activates sterilization module (156) to apply a sterilant (block 314) in sterilization chamber (152). This stage of the process may be referred to as the "transfer phase." By way of example only, the sterilant may comprise a vapor of oxidizing agent such as hydrogen peroxide, peroxy acids (e.g. peracetic acid, performic acid, etc.), ozone, or a mixture thereof. Furthermore, the sterilant may comprise chlorine dioxide. Various other suitable forms that the sterilant may take are described herein; while other forms will be apparent to those of ordinary skill in the art in view of the teachings herein. It should also be understood that, in some versions, the sterilant may be applied (block 314) in different ways based on the user's selection of cycle (block 200) as described above.

Once the sterilant has been applied (block 314) to sterilization chamber (152), processor (162) monitors the time (block 316) to determine whether a sufficient, predetermined duration has passed. By way of example only, this predetermined duration may be anywhere from a few seconds to several minutes. Until the predetermined duration has passed, sterilization chamber (152) remains in a sealed state at the above-noted predetermined pressure level, with the applied sterilant acting upon the medical device(s) contained within sterilization chamber (152). In some variations, processor (162) may monitor data from one or more pressure sensors within sterilization chamber (152) to conform whether a sufficient vacuum pressure is being maintained within sterilization chamber (152).

After the predetermined duration has passed, processor (162) activates (block 318) venting valve (182) to vent sterilization chamber (152) to atmosphere. In some versions, sterilization chamber (152) is allowed to reach atmospheric pressure, while in other versions sterilization chamber (152) only reaches sub-atmospheric pressure. The venting stage of the process may be referred to as the "diffusion phase." In the present example, the sterilization cycle is then complete (block 320) after completion of the diffusion phase. In some other instances, vacuum is again applied to sterilization chamber (152) after completion of the diffusion phase; and then a plasma is applied to sterilization chamber (152). It should be understood that the entire sterilization cycle shown in FIG. 3 (including the above-noted variation where a subsequent vacuum then sterilization are applied) may be repeated one or more times after being completed once. In other words, a medical device may remain within sterilization chamber (152) and experience two or more iterations of the entire cycle shown in FIG. 3 (including the above-noted variation where a subsequent vacuum then sterilization are applied). The number of iterations may vary based on the cycle selection (block 200), which may be influenced by the particular kind of medical device that is being sterilized in sterilization chamber (152).

Upon completion of the sterilization cycle (block 208), sterilization cabinet (150) may cycle the results (block 210) of the sterilization cycle (block 208). For instance, if sterilization cycle (block 208) was canceled or unable to complete due to error or by a user action, sterilizing cabinet (150) may remain sealed and may also display a sterilization cycle cancellation message via touch screen display (160); as well as various details relating to the sterilization cycle, such as date, time, configuration, elapsed time, sterilization cycle operator, the stage at which the sterilization cycle failed, and other information that may be used to identify why the sterilization cycle. If sterilization cycle (block 208) is completed successfully, sterilization cabinet (150) may display a notification via touch screen display (160) indicating successful completion of sterilization cycle (block 208). In addition, sterilization cabinet (150) may display information such as sterilization cycle identifier, sterilization cycle type, start time, duration, operator, and other information (666).

In some variations, a pre-plasma may be applied in the sterilization cycle (block 208) to heat up the medical device contained in sterilization chamber (152). By way of example only, plasma may be applied between applying a vacuum (block 310) and applying sterilant (block 314). In addition, or in the alternative, a post-plasma may be applied at the end of sterilization cycle (block 208) to degrade any residual sterilant that may be adsorbed to the surface of the medical device contained in sterilization chamber (152). It should be understood that, before applying the post-plasma, a vacuum would first need to be applied to sterilization chamber (152).

By way of example only, the process depicted in FIG. 3 may be carried out at temperatures where the walls of sterilization chamber (152) are between about 30° C. and about 56° C., or more particularly between about 47° C. and about 56° C., or even more particularly about 50° C.; and where the temperature of the medical device in sterilization chamber (152) is between about 5-10° C. and about 40-55° C.

In addition to the foregoing, sterilizing cabinet (150) may be configured to perform sterilization processes in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein.

While the foregoing examples are described in the context of sterilizing medical devices, and particularly endoscopes, it should be understood that the teachings herein may also be readily applied in the context of sterilizing various other kinds of articles. The teachings are not limited to endoscopes or other medical devices. Other suitable articles that may be sterilized in accordance with the teachings herein will be apparent to those of ordinary skill in the art.

III. Overview of Exemplary Cartridge

Figure 4:
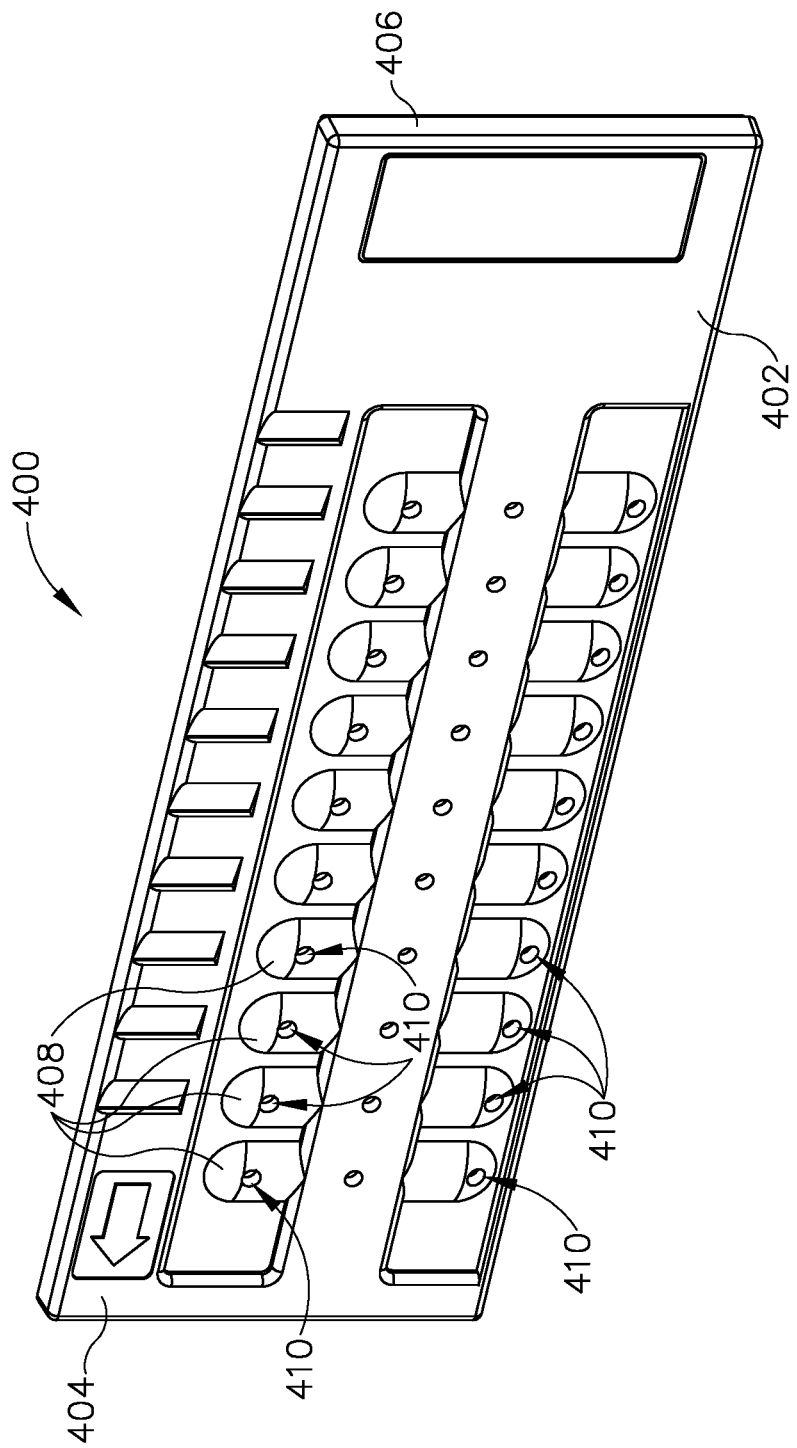
FIG. 4 depicts a perspective view of an exemplary cartridge that may be readily used in the sterilizing cabinet of FIG. 1.
Figure 5:
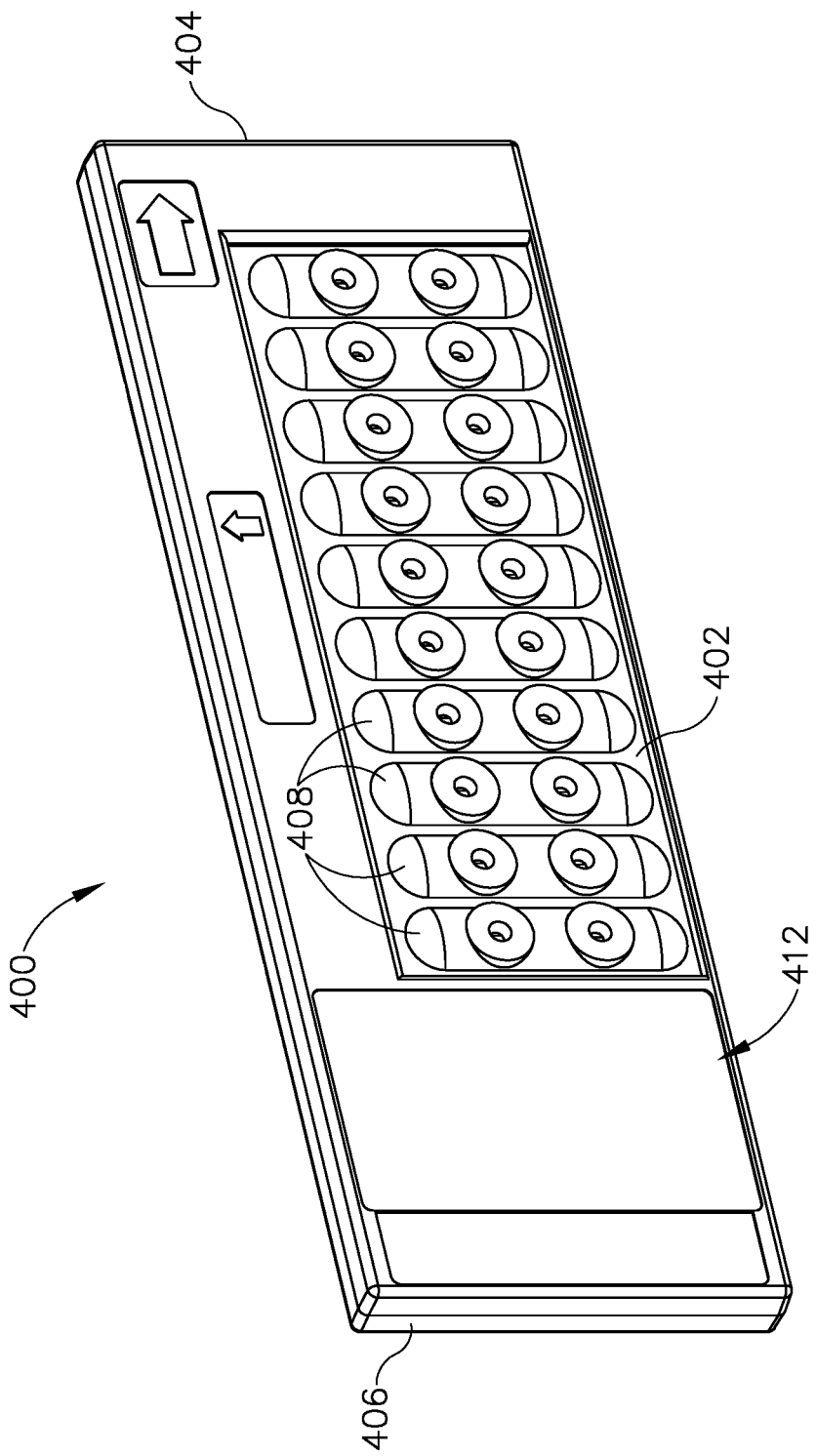
FIG. 5 depicts a perspective view of the cartridge of FIG. 4.

As mentioned above, sterilizing module (156) is configured to receive replaceable sterilant cartridges (158) containing a certain amount of sterilant in order to dispense sterilant into sterilization chamber (152). In turn, sterilization chamber (152) may utilize sterilant from replaceable sterilant cartridges (158) in order to sterilize medical devices contained within sterilization chamber (152). FIGS. 4-5 show an exemplary form that sterilant cartridge (158) may take. In particular, FIGS. 4-5 show a sterilant cartridge (400) that may be readily used in sterilizing module (156).

Sterilant cartridge (400) of the present example includes a body (402) extending from a proximal end (406) to a distal end (404). Body (402) defines a plurality of individual reservoir cells (408). Each reservoir cell (408) may contain a predetermined amount of sterilant that may be isolated from sterilant in other reservoir cells (408). Each reservoir cell (408) also defines a pair of access recesses (410). Access recesses (410) are configured to store sterilant in reservoir cells (408), but are also penetrable in order to remove sterilant from reservoir cells (408). As will be described in greater detail below, an extraction assembly may selectively remove sterilant from reservoir cells (408) via access recesses (410). While in the current example, there are a plurality of reservoir cells (408) within a single cartridge (400), it should be understood that one reservoir cell (408) may be present or any other suitable number of reservoir cells (408) as would be apparent to one having ordinary skill in the art in view of the teachings herein.

As best seen in FIG. 5, body (402) of sterilant cartridge (400) also includes an information area (412). Information area (412) may contain information that may be read by other equipment on sterilizing module (156) in order to communicate such information to processor (162). Information area (412) may contain readable information relevant to sterilant cartridge (400), such as the expiration date of sterilant within cartridge (400), whether or not sterilant cartridge (400) has already been used before, or any other suitable information that would be apparent to one having ordinary skill in the art in view of the teachings herein. By way of example only, information area (412) may include a barcode, a QR code, and/or any other optically readable indicia; an RFID tag; and/or any other suitable kind of machine readable indicia.

IV. Exemplary Cartridge Processing Assembly

Figure 6:
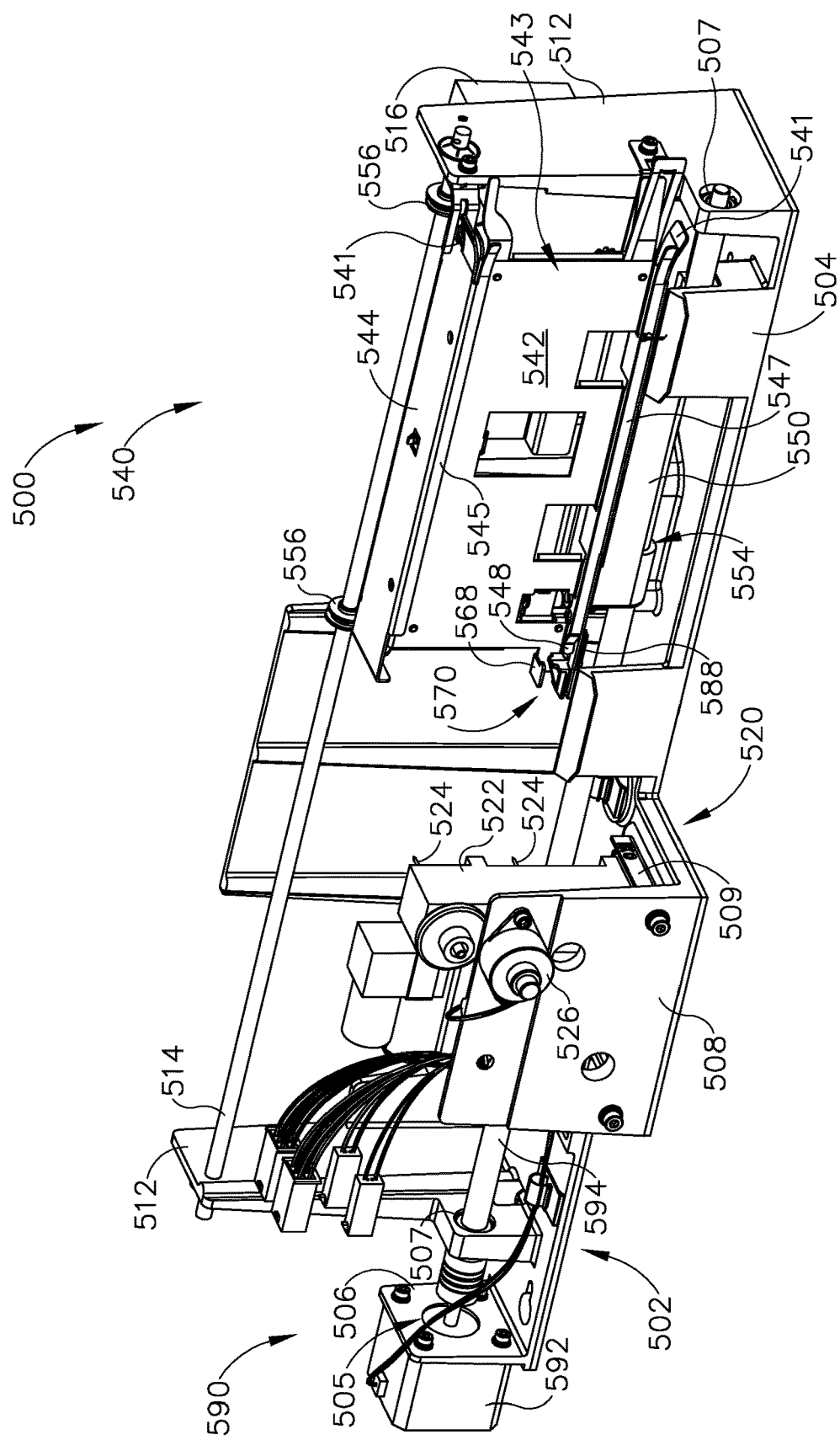
FIG. 6 depicts a perspective view of an exemplary cartridge processing assembly that may be readily incorporated into the sterilizing cabinet of FIG. 1.
Figure 7:
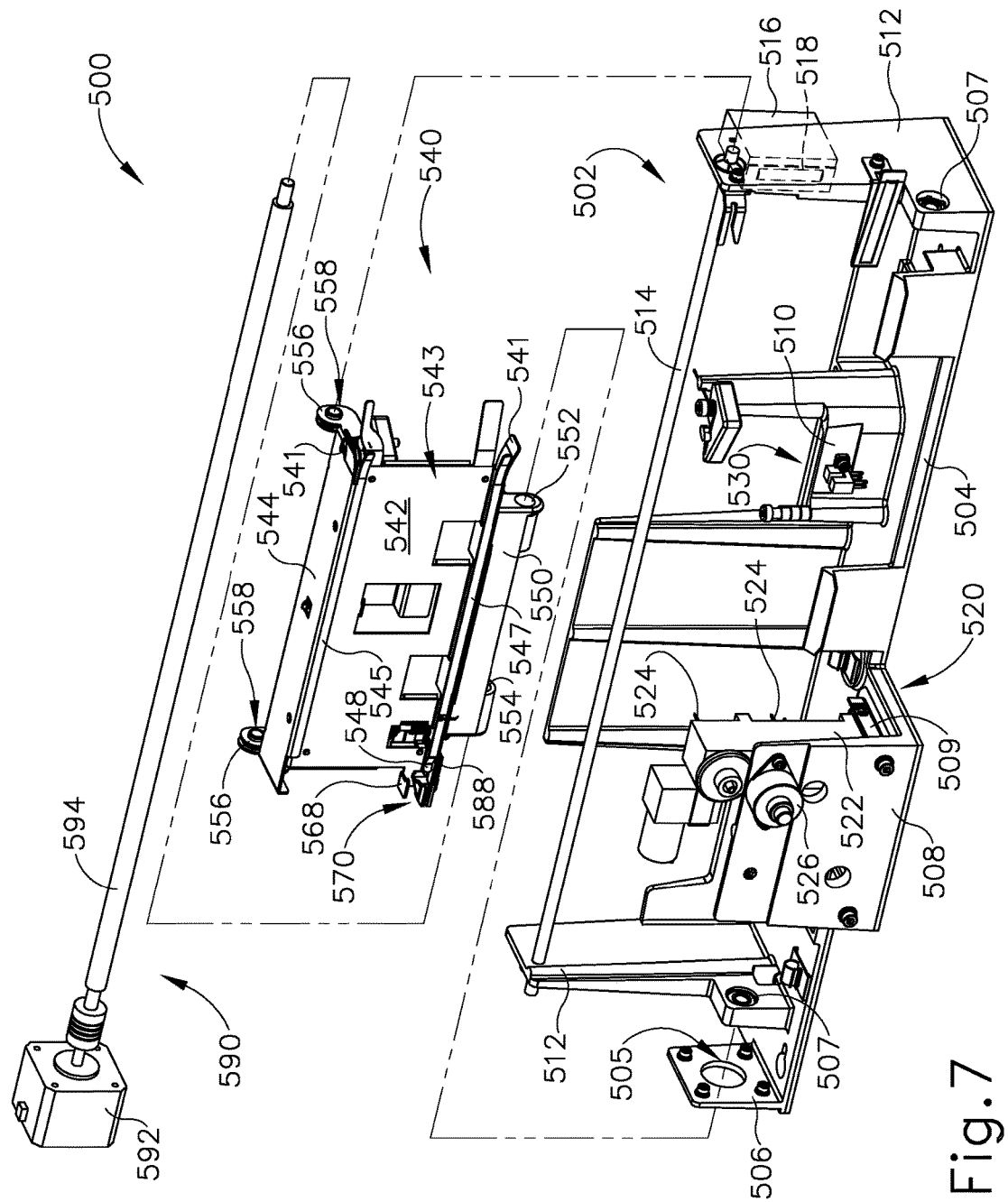
FIG. 7 depicts an exploded perspective view of the cartridge processing assembly of FIG. 6.

FIGS. 6-7 show an exemplary cartridge processing assembly (500) that may be readily incorporated into sterilizing module (156) described above. Therefore, it should be understood that any suitable portions of cartridge processing assembly (500) may be in communication with processor (162), such that processor (162) may receive information from, and send instructions to, selected portions of cartridge processing assembly (500). Such communication may be established through any suitable means as would be apparent to one having ordinary skill in the art in view of the teachings herein. For example, wireless or wired communication may be utilized. It should also be understood that selected portions of cartridge processing assembly (500) may be in fluid communication with other suitable components of sterilizing cabinet (150), such as sterilization chamber (152). Such fluid communication may be established through any suitable means as would be apparent to one having ordinary skill in the art in view of the teachings herein.

Cartridge processing assembly (500) is configured to receive a replaceable sterilant cartridge (400), read information stored on replaceable sterilant cartridge (400) to confirm cartridge (400) is usable, and actuate cartridge (400) and portions of cartridge processing assembly (500) to extract sterilant from individual reservoir cells (408). In some instances, an operator may insert cartridge (400) into cartridge processing assembly (500) at an incorrect angle and/or with too much force. In some such instances, cartridge (400) may inadvertently actuate selected portions of cartridge processing assembly (500), thereby misaligning some actuating portions of cartridge processing assembly (500) and/or cartridge (400). In some other instances, an operator may improperly insert cartridge (400) into cartridge processing assembly (500) through other improper techniques, thereby misaligning some actuating portions of cartridge processing assembly (500) and/or cartridge (400). Therefore, it may be desirable to confirm that cartridge (400) has been properly inserted into cartridge processing assembly (500), without misaligning some actuating portions of cartridge processing assembly (500) or cartridge (400) itself. It may further be desirable to actively prevent cartridge (400) from misaligning some actuating portion of cartridge processing assembly (500).

Cartridge processing assembly (500) of the present example includes a frame assembly (502), an extraction assembly (520), a sensor assembly (530), a carriage assembly (540), and a carriage actuation assembly (590). Frame assembly (502) includes a body (504) including a motor mount (506), an extraction mount (508), a sensor mount (510), rail supports (512), a slide rail (514), and an ID reader body (516) housing an ID reader sensor (518). Motor mount (506) in configured to affix to a motor (592) of carriage actuation assembly (590). Motor mount (506) also defines a bore (505) that is configured to receive a lead screw (594) extending from motor (592). Body (504) also includes rotational bearings (507) that are configured to rotationally support lead screw (594) such that lead screw (594) may rotate about its own longitudinal axis relative to body (504).

Extraction mount (508) is configured to affix to a selected portion of extraction assembly (520) in order to support extraction assembly (520). Extraction mount (508) includes a slide slot (509) that is configured to act as a guide for actuating portions of extraction assembly (520). Sensor mount (510) is configured to affix to sensor assembly (530) such that sensor assembly (530) is fixed relative to body (504) of frame assembly (502). As will be described in greater detail below, sensor assembly (530) is fixed relative to frame assembly (502) in order to verify that cartridge (400) and carriage assembly (540) are properly aligned relative to each other and to frame assembly (502). Slide rail (514) extends along body (504) and is attached to rail supports (512). As will be described in greater detail below, slide rail (514) slidably couples with a portion of carriage assembly (540).

ID reader body (516) houses ID reader sensor (518). ID reader sensor (518) is in communication with processor (162). ID reader sensor (518) may be substantially similar to identification tag reader (166) described above. ID reader sensor (518) may read any suitable information associated with cartridge (400) inserted into cartridge processing assembly (500) and send that information to processor (162). ID reader sensor (518) may read information relating to the expiration date of cartridge (400) or determine if cartridge (400) has been previously used. If processor (162) receives information indicating that cartridge (400) is past its expiration date or has been previously used, processor (162) may direct cartridge processing assembly (500) to eject cartridge (400) such that cartridge (400) may not be used. Of course, any other suitable information may be read by ID reader sensor (518), which may be communicated to processor (162) for any other suitable functions as would be apparent to one having ordinary skill in the art in view of the teachings herein. It should be understood that ID reader sensor (518) may be positioned and configured to automatically read information presented on (412); and that this reading may automatically occur when cartridge (400) is inserted into carriage assembly (540).

Figure 16A:
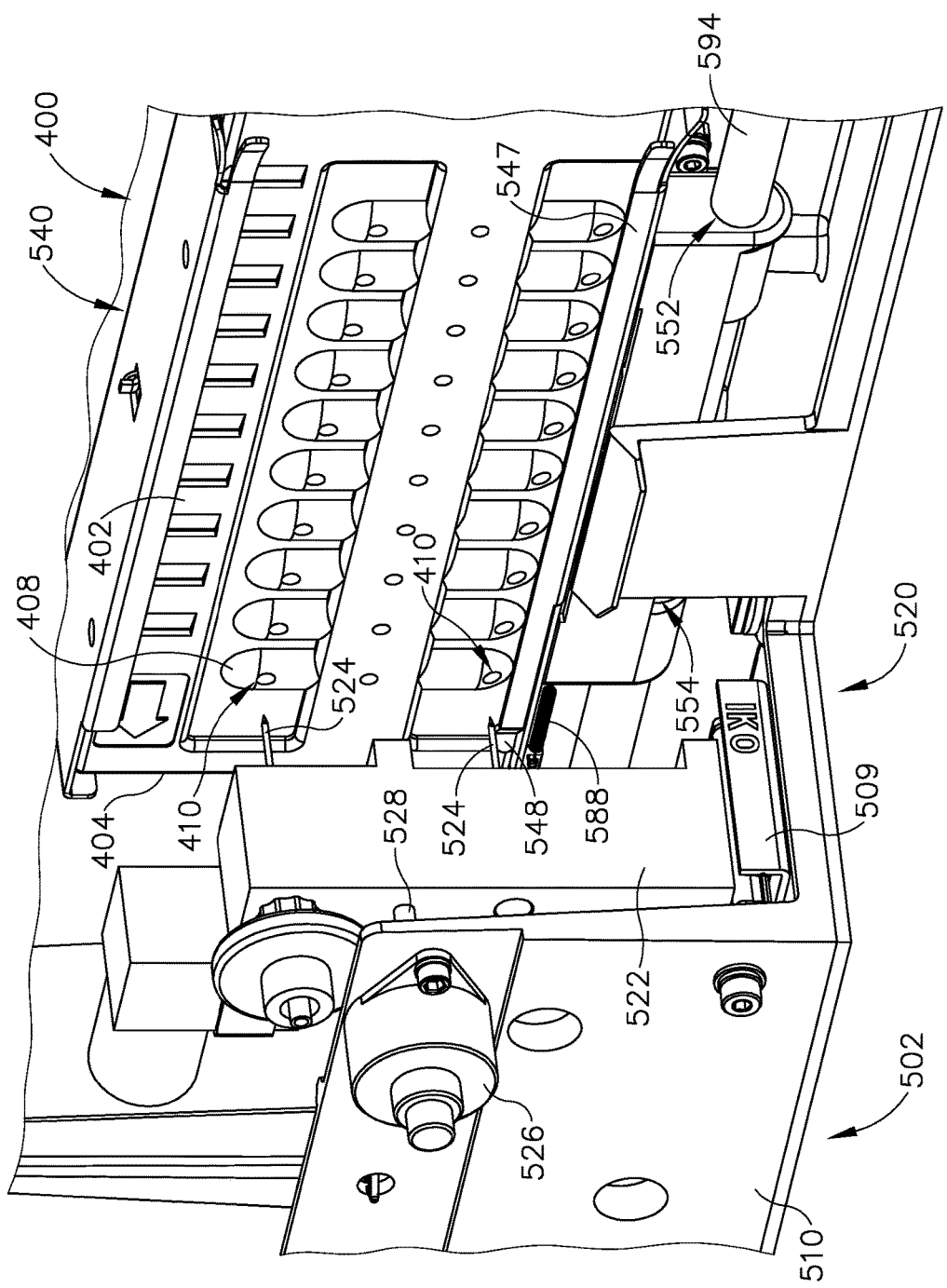
FIG. 16A depicts a perspective view of an exemplary sterilant extraction assembly of the cartridge processing assembly of FIG. 6 aligned relative to the cartridge of FIG. 4.

As best seen in FIGS. 16A-16B, extraction assembly (520) includes an extraction mechanism (522), a pair of needles (524) attached to extraction mechanism (522), an actuator (526), and a shaft (528) coupled to both extraction mechanism (522) and actuator (526). As will be described in greater detail below, extraction assembly (520) may be used to remove sterilant from reservoir cells (408) of cartridge (400).

Actuator (526) is attached to extraction mount (508) and is in communication with processor (162). Actuator (526) is configured to move shaft (528) and extraction mechanism (522) relative to frame assembly (502). Therefore, processor (162) may instruct actuator (526) to move shaft (528) and extraction mechanism (522) relative to frame assembly (502). By way of example only, actuator (526) may comprise a solenoid. Other suitable forms that actuator (526) may take will be apparent to those of ordinary skill in the art in view of the teachings herein.

Extraction mechanism (522) is in fluid communication with needles (524) and may also be in fluid communication with sterilization chamber (152). Extraction mechanism (522) is configured to remove sterilant from cartridge (400) with needles (524) and transport sterilant to sterilization chamber (152). Extraction mechanism (522) may include air pumps, valves, and any other suitable components to extract sterilant from cartridge (400) as would be apparent to one having ordinary skill in the art in view of the teachings herein. Extraction mechanism (522) may also be in communication with processor (162) to selectively activate mechanics of extraction mechanism (522).

Extraction mechanism (522) is slidably coupled with slide rail (514) such that when actuator (526) is activated, extraction mechanism (522) slides within slide rail (514). As best seen between FIGS. 16A-16B, when cartridge (400) is properly aligned with access recesses (410) of reservoir cell (408), actuator (526) may drive extraction mechanism (522) toward cartridge (400) such that needles (524) penetrate access recesses (410) of reservoir cell (408). Processor (162) may then activate mechanics of extraction mechanism (522) in order to remove sterilant from reservoir cell (408) and transfer the sterilant to other suitable portions of sterilizing cabinet (150) as would be apparent to one having ordinary skill in the art in view of the teachings herein.

Carriage actuation assembly (590) includes motor (592) and lead screw (594). Motor (592) is configured to rotate lead screw (594) about the longitudinal axis of lead screw (594). As will be described in greater detail below, threading of lead screw (594) meshes with complementary threading of carriage assembly (540) such that rotation of lead screw (594) drives longitudinal translation of carriage assembly (540) along the longitudinal axis of lead screw (594). Since motor (592) may rotate lead screw (592), motor (592) may then longitudinally drive carriage assembly (540) relative to frame assembly (502) via lead screw (594). At times when frame assembly (502) should be held stationary, processor (162) may activate motor (592) to provide electric motor braking, which may prevent unintended rotation of lead screw (594), and therefore prevent unintended translation of carriage assembly (540). For example, if electric motor braking is not provided via motor (592), longitudinal forces acting on carriage assembly (540), such as excess force provided by an operator inserting cartridge (400) into carriage assembly (540), may cause frictional engagement between complementary threading of carriage assembly (540) and lead screw (592). Frictional engagement between complementary threading may lead to unintended rotation of lead screw, leading to unintended translation of carriage assembly (540). When electric braking is applied via motor (592), such longitudinal forces acting on carriage assembly (540) may not be strong enough to accidentally rotate lead screw (592) and translate carriage assembly (540). Various suitable ways in which electric braking may be applied via motor (592) will be apparent to those of ordinary skill in the art in view of the teachings herein. It should also be understood that mechanical braking may be used in addition to, or in lieu of, using electric motor braking.

Motor (592) may be in communication with processor (162) such that motor (592) may receive instructions from processor (162). By way of example only, motor (592) may comprise a stepper motor or any other suitable motor assembly that would be apparent to one having ordinary skill in the art in view of the teachings herein. Motor (592) may contain any suitable number of components that would be apparent to one having ordinary skill in the art in view of the teachings herein. Processor (162) may store its previous instructions to rotate motor (592) such that processor (162) may infer the rotational position of motor (592) based on previous instructions, and therefore processor (162) may infer the rotational position of lead screw (594). Alternatively, motor (592) may have a rotational sensor (e.g., encoder assembly) that is configured to communicate the rotational position of lead screw (594) to processor (162). Of course, any other suitable rotational position measurement device may be used as would be apparent to one having ordinary skill in the art in view of the teachings herein.

If carriage assembly (540) and cartridge (400) are properly inserted and located relative to frame assembly (502), the rotational position of lead screw (594) may correlate to a longitudinal position of carriage assembly (540) relative to frame assembly (502). Therefore, processor (162) may accurately predict the longitudinal position of carriage assembly (540) based on the rotational position of lead screw (594) if carriage assembly (540) is properly located. In turn, processor (162) may instruct motor (592) to rotate lead screw (594) in order to translate carriage assembly (540) and a properly inserted cartridge (400) such that cartridge (400) is properly aligned with extraction assembly (520) in order to remove sterilant from reservoir cells (408) in a precise succession as described above.

It may be desirable to confirm the location of a carriage assembly (540) and a newly inserted cartridge (400) before utilizing motor (592) to align cartridge (400) with extraction assembly (520) in order to remove sterilant from reservoir cells (408). If carriage assembly (540) and/or cartridge (400) are/is not properly aligned, extraction assembly (520) may not properly align with cartridge (400) when attempting to remove sterilant via needles (524) penetrating access recesses (410). If needles (524) do not align with access recesses (410), needles (524), cartridge (400), extraction mechanism (524), other components of extraction assembly (520), and/or cartridge processing assembly (500) may be damaged. Therefore, it may be desirable to accurately locate a newly inserted cartridge (400) relative to carriage assembly (540) and frame assembly (502), and locate carriage assembly (540) relative to frame assembly (502), with ensured consistency. The following description relates to exemplary components and techniques that may be used to ensure consistency in the accurate location of newly inserted cartridge (400) relative to carriage assembly (540) and frame assembly (502); and of carriage assembly (540) relative to frame assembly (502).

A. Exemplary Sensor Assembly

Figure 8:
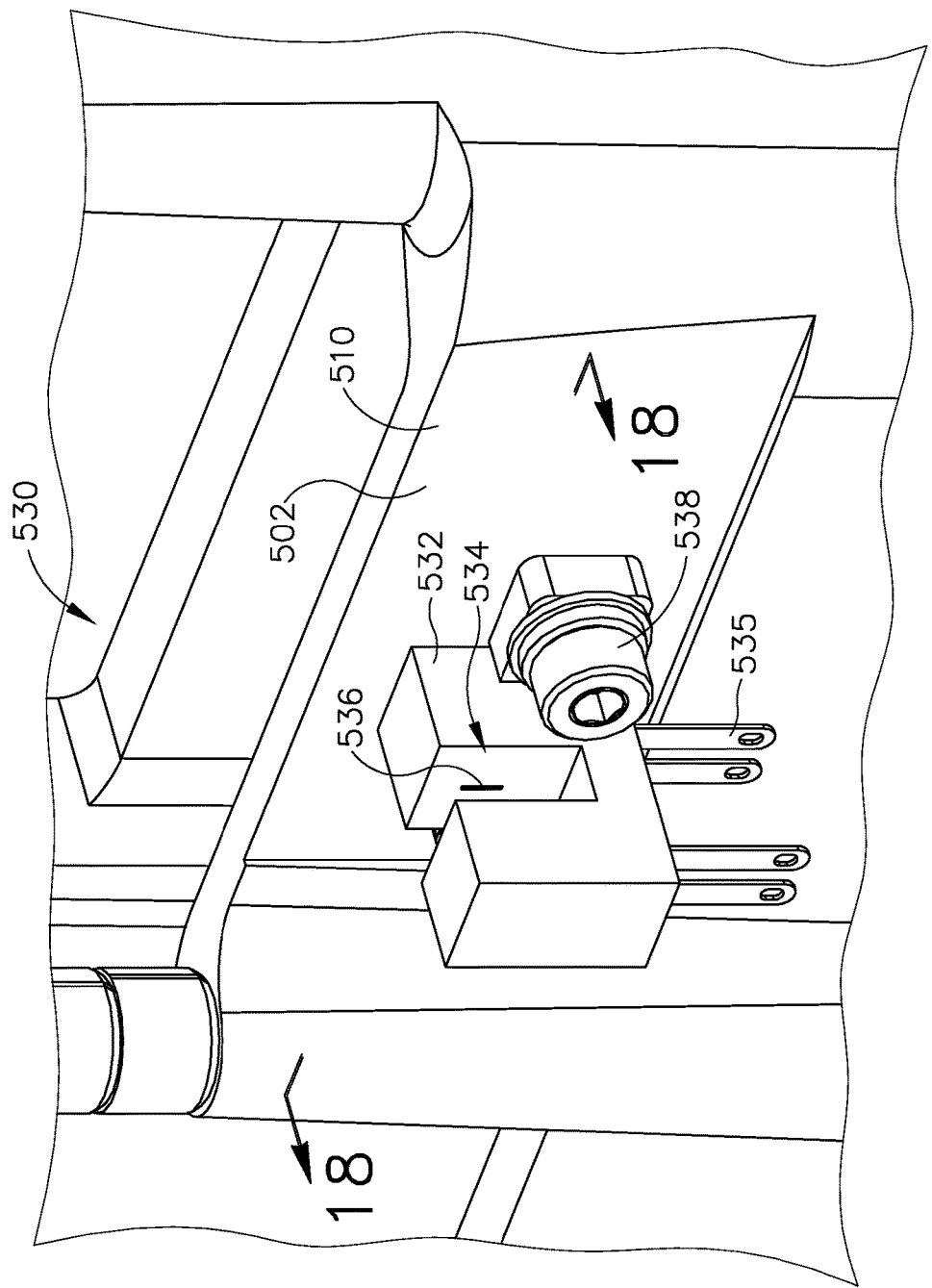
FIG. 8 depicts a perspective view of an exemplary sensor assembly of the cartridge processing assembly of FIG. 6.
Figure 9:
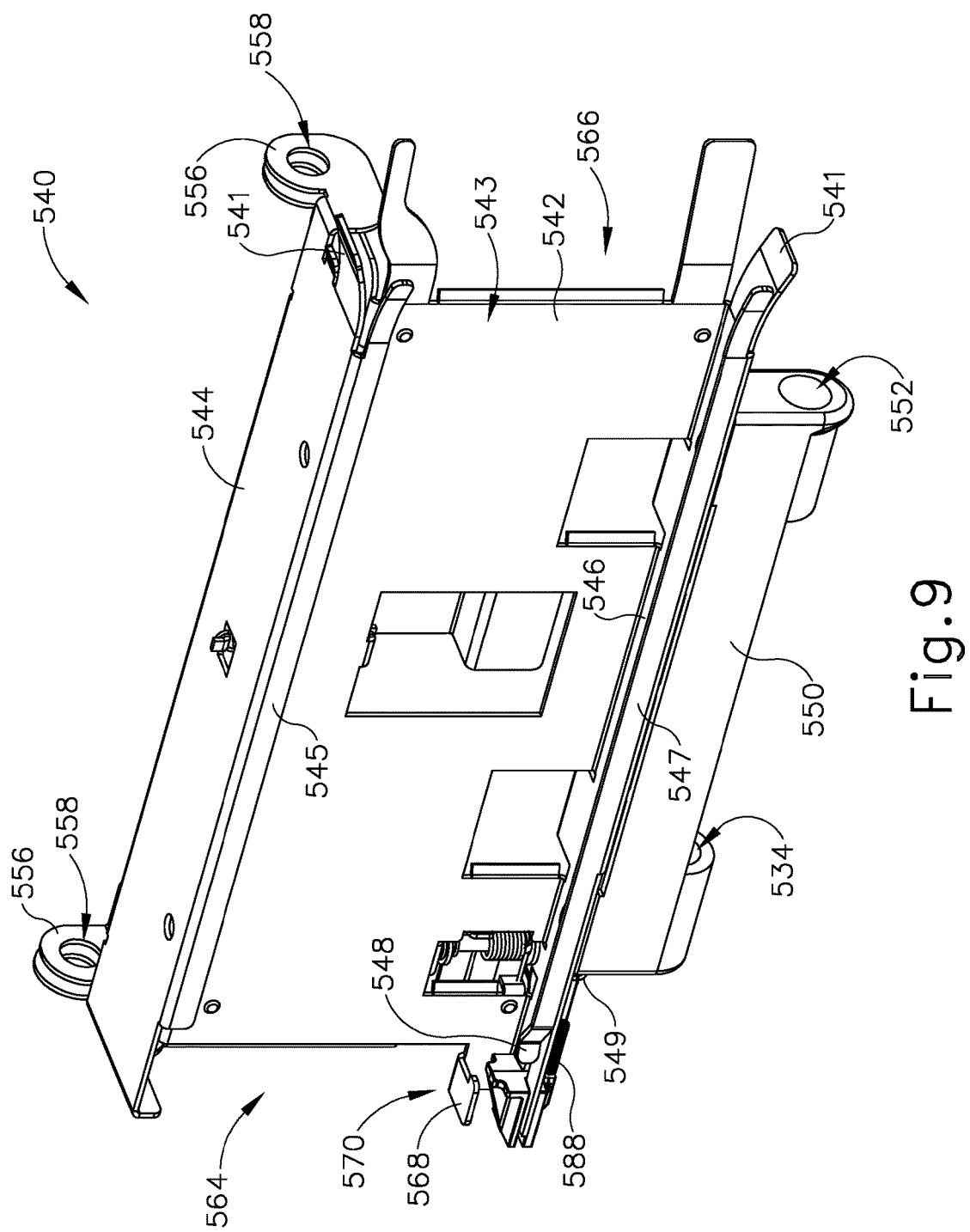
FIG. 9 depicts a perspective view of an exemplary carriage assembly of the cartridge processing assembly of FIG. 6.
Figure 10:
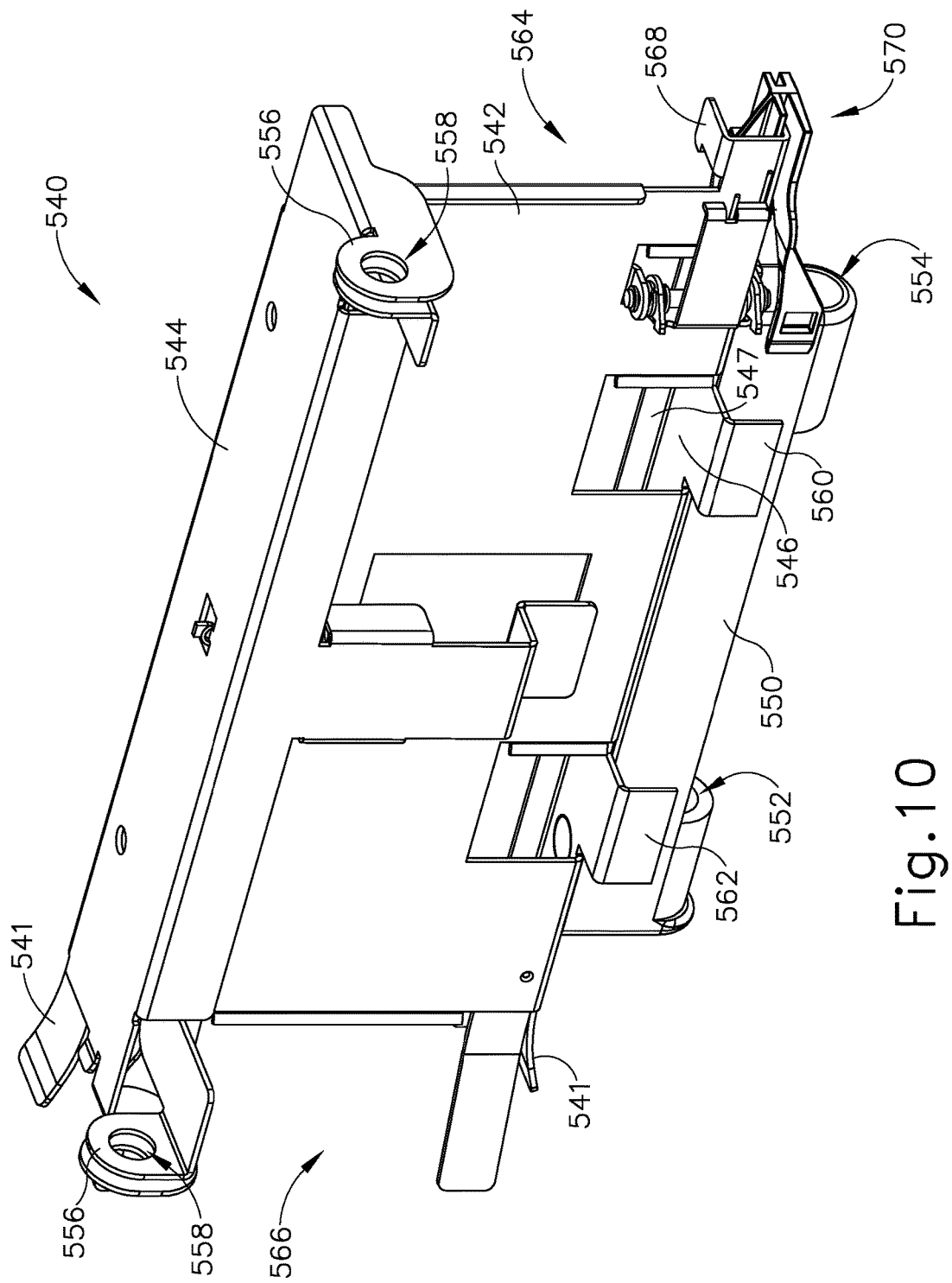
FIG. 10 depicts another perspective view of the carriage assembly of FIG. 9.

As best shown in FIG. 8, sensor assembly (530) of the present example includes a housing (532) defining a U-shaped channel (534), opposing optical sensors (536) located within U-shaped channel (534), a mount (538), and electrical contacts (535). Housing (532) is fixed relative to sensor mount (510) via mount (538). Electrical contacts (535) are configured to provide communication between optical sensors (536) and processor (162). It should be understood that wires (not shown) may extend between electrical contacts (535) and processor (162) to provide such communication.

Housing (532) is located within frame assembly (502) such that U-shaped channel (534) may accept selected portions of carriage assembly (540) when portions of carriage assembly (540) actuate relative to frame assembly (502). Optical sensors (536) are placed on opposite sides of U-shaped channel (534) of housing (352) such that optical sensors (536) face toward each other. Optical sensors (536) are configured to detect when a portion of carriage assembly (540) is located within U-shaped channel (534) of housing (532) and between optical sensors (536). Optical sensors (536) may communicate with processor (162) when a portion of carriage assembly (540) is detected between optical sensors (536); as well as when a portion of carriage assembly (540) is not detected between optical sensors (536). Therefore, optical sensors (536) may act as a trigger for processor (162) to initiate an action based on the presence or absence of an object between optical sensors (536). As will be described in greater detail below, processor (162) may utilize signals from optical sensors (536) in order to execute a cartridge and carriage locating process, as well as a homing process in preparation for extracting sterilant from cartridge (400). Processor (162) may also utilize signals from optical sensors (536) to start and stop other actions/ functions, such as counting rotational displacement of motor (592). In other words, optical sensors (536) may start and stop a counting process of processor (162).

While optical sensors (536) are used in the present example to detect the presence of objects between U-shaped channel (534), any other suitable trigger mechanism may be used. For example, a biased camming trigger may be located within U-shaped channel (534) such that as carriage assembly (540) travels through U-shaped channel (534), portions of carriage assembly (540) cam against the biased camming trigger to signal that an object is located within housing (532). Other suitable kinds of sensors that may be used will be apparent to those of ordinary skill in the art in view of the teachings herein.

B. Exemplary Carriage Assembly

As best seen in FIGS. 9-12, carriage assembly (540) extends from a proximal portion (566) to a distal portion (564). Carriage assembly (540) includes a side panel (542), a top panel (544), a bottom panel (546), a nut (550) fixed to the underside of bottom panel (546), a translating flag (570) slidably coupled to bottom panel (546), and a first and second static flag (560, 562) extending downwardly from bottom panel (546). As will be described in greater detail below, translating flag (570), first static flag (560), and second static flag (562) are configured to translate through U-shaped channel (534) of sensor assembly (530) in order to provide verification of proper insertion of cartridge (400) into carriage assembly (540), to verify that carriage assembly (540) is properly located within cartridge processing assembly (500), and to properly home carriage assembly (540) and inserted cartridge (400) in preparation for an extraction process.

Side flange (542) includes a cartridge stop (568) located at distal portion (564) of carriage assembly (540). Top panel (544) includes a downwardly extending flange (545) extending from an edge of top panel (544) and a proximally presented flange (541). Additionally, bottom panel (546) includes an upwardly extending flange (547) extending from an edge of bottom panel (546) and a proximally presented flange (541). Upwardly extending flange (547) includes a leaf spring (548) terminating at distal portion (564) of carriage assembly (540). Side panel (542), top panel (544), bottom panel (546), downwardly extending flange (545), and upwardly extending flange (547) together define cartridge channel (543). As best seen between FIGS. 15A-15B, cartridge channel (543) is open at proximal portion (566) of carriage assembly (540) in order to receive distal end (404) of cartridge (400). Proximally presented flanges (541) may accommodate insertion of distal end (404) of cartridge (400) and provide guiding lead-ins for cartridge (400) such that cartridge (400) does not necessarily need to be entirely aligned with cartridge channel (543) during initial insertion of cartridge (400). Cartridge stop (568) is configured to prevent distal end (404) of cartridge (400) from sliding past cartridge stop (568). Leaf spring (548) is configured to push adjacent portions of cartridge (400) laterally against side panel (542) in order to ensure cartridge (400) is pressed against side panel (542) when cartridge (400) is properly inserted.

Top panel (544) includes two flanges (556) each defining an opening (558). Openings (558) are dimensioned to slidably receive slide rail (514) such that carriage assembly (540) may translate along the path defined by slide rail (514).

Figure 11:
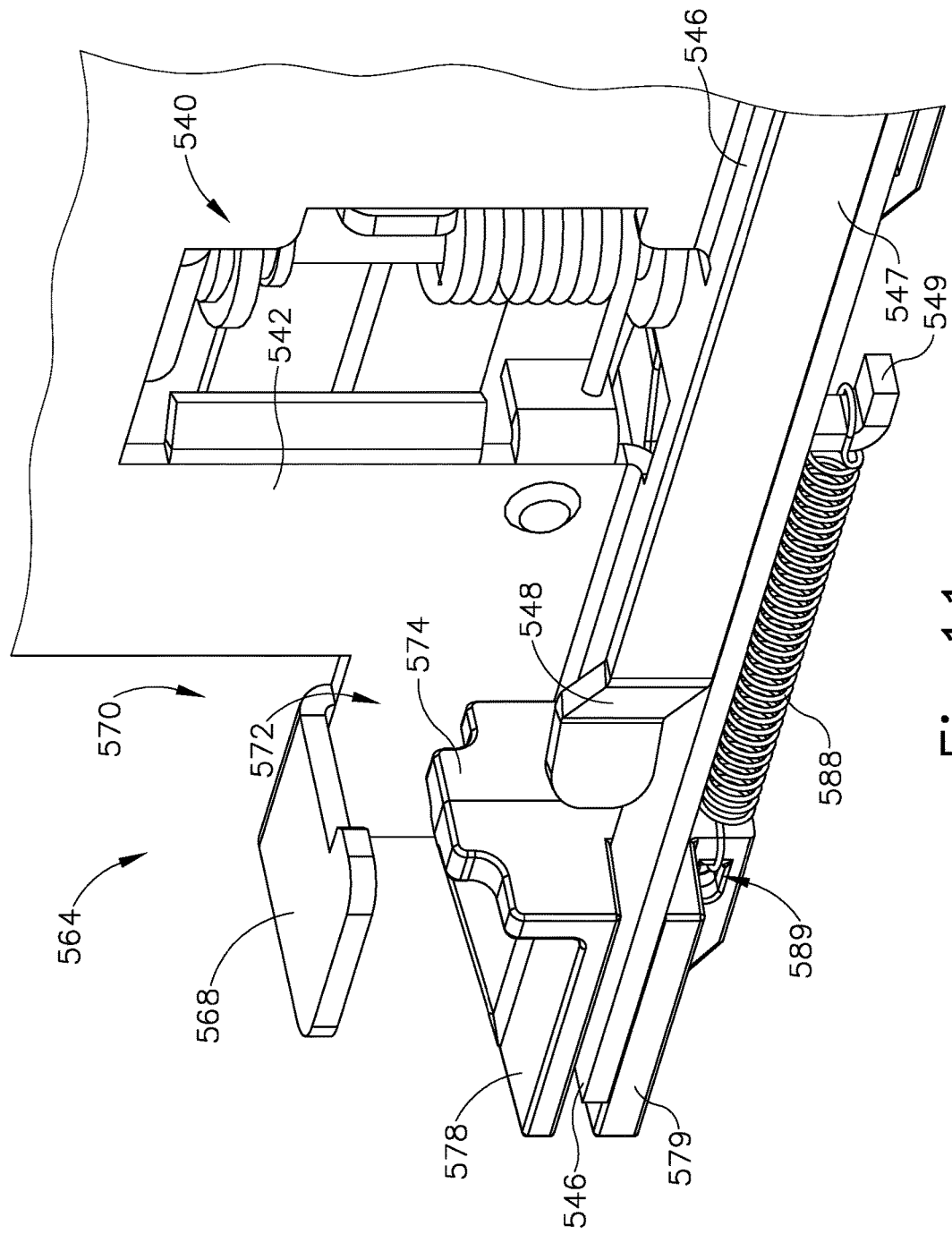
FIG. 11 depicts a perspective view of a distal portion of the carriage assembly of FIG. 9.
Figure 12:
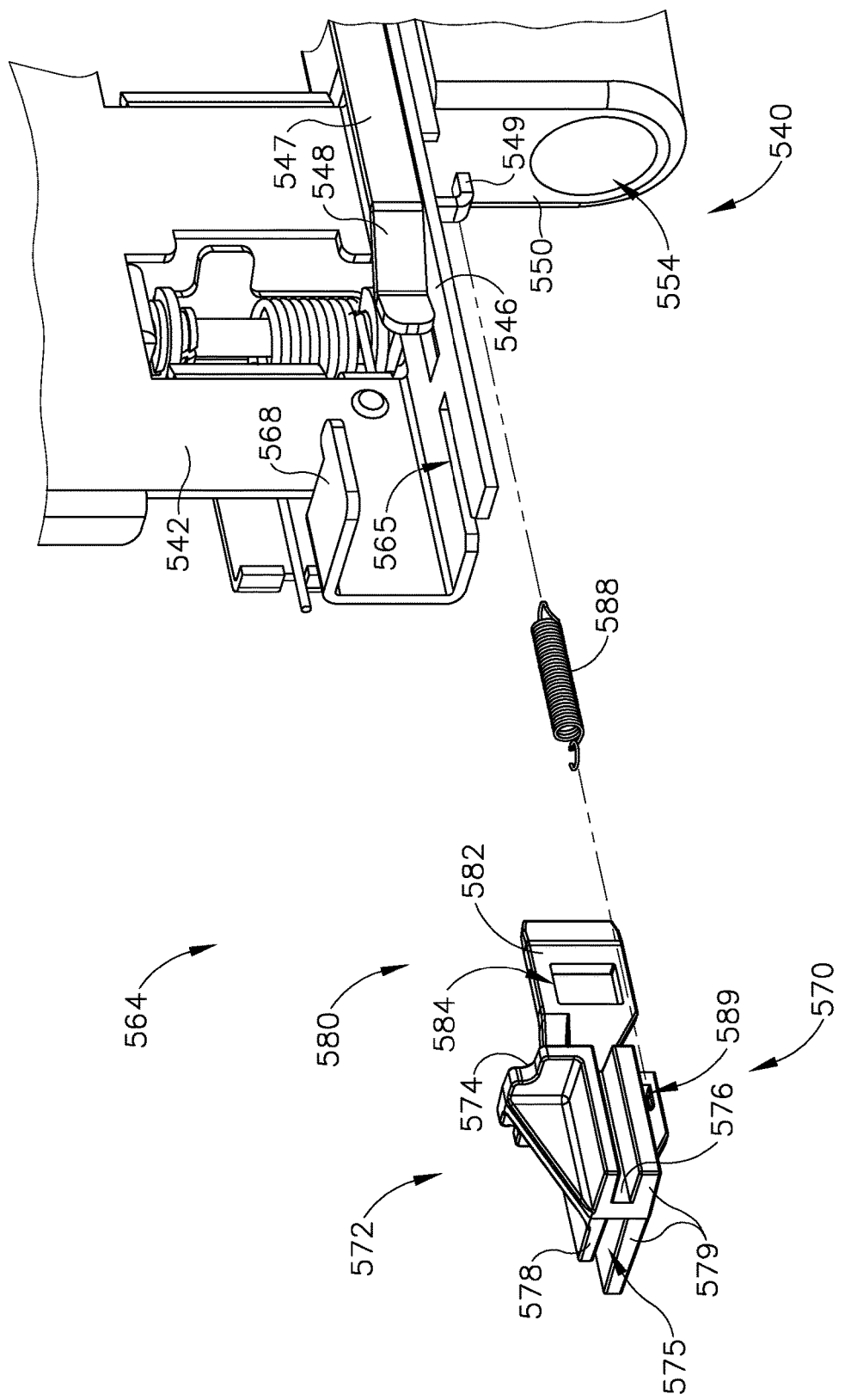
FIG. 12 depicts an exploded perspective view of the distal portion of the carriage assembly of FIG. 9.

As best seen in FIGS. 11-12, nut (550) includes a distally presented hook (549), which is configured to couple with bias spring (588). As will be described in greater detail below, bias spring (588) connects with translating flag (570) in order to bias translating flag (570) relative to the rest of carriage assembly (540) toward a proximal position. Nut (550) also defines a proximal bore (552) and a distal threaded bore (554). Proximal bore (552) and distal threaded bore (554) are dimensioned to receive lead screw (594). In particular, threaded bore (554) includes complementary threading with the thread of lead screw (594) such that rotation of lead screw (594) longitudinally drives nut (550) and the rest of carriage assembly (540) along the longitudinal axis of lead screw (594). Because carriage (540) is coupled with slide rail (514) via flanges (556), carriage assembly (540) does not rotate in response to rotation of lead screw (594). In other words, flanges (556) and slide rail (514) rotationally fix carriage assembly (540) while allowing translation of carriage assembly (540), such that frictional engagement between complementary threading of lead screw (594) and threaded bore (554) only translate carriage assembly (540). While in the current example, distal bore (554) is threaded and proximal bore (552) is not, any suitable combination of threaded bores may be utilized as would be apparent to one having ordinary skill in the art in view of the teachings herein. For example, both bores (552, 554) may be threaded; or only proximal bore (552) may be threaded.

As best seen in FIGS. 11-14, translating flag (570) includes a coupling portion (572) and a flag portion (580) coupled to each other with a laterally offset arm (585). As described above, and as will be described in greater detail below, a portion of translating flag (570) is configured to translate through U-shaped channel (534) of sensor assembly (530). In particular, flag portion (580) is configured to translate through U-shaped channel (534) of sensor assembly (530). Additionally, as described above, translating flag (570) is configured to translate relative to the rest of carriage assembly (540), including static flags (560, 562). As will be described in greater detail below, translating flag (570) and static flags (560, 562) may be utilized to compare the placement of an inserted cartridge (400) relative to carriage assembly (540); and to verify the proper location of carriage assembly (540) along lead screw (594).

Coupling portion (572) includes a contact wall (574), a narrow member (576), an upper lateral projection (578), and a lower lateral projection (579). As will be described in greater detail below, coupling portion (572) is configured to slidably couple with bottom panel (546) of carriage assembly (540). Narrow member (576), upper lateral projection (578), and lower lateral projection (579) define a guide path (575) that is configured to receive a portion of bottom panel (546) defining a slot (565). In particular, narrow member (576) is configured to slide within slot (565) while upper later projection (578) and lower lateral projection (579) rest on the top and bottom faces of bottom panel (546), respectively. Coupling portion (572) also defines a coupling hole (589) configured to couple with bias spring (588). As described above, one end of bias spring (588) is configured to couple with hook (549) of nut (550) such that bias spring (588) may bias translating flag (570) to the proximal position within slot (565), as best seen in FIG. 11. Narrow portion (576) abuts against the proximal end of slot (565) defined by bottom panel (546) when translating flag (270) is in the proximal position. As will be described in greater detail below, translating flag (570) is configured to translate distally within slot (565) of bottom panel (546) in response to cartridge (400) being inserted within cartridge channel (543) of carriage assembly (540). In particular, translating flange (570) may translate within slot (565) in response to distal end (404) of cartridge (400) bearing against contact wall (574) of translating flag (570).

Figure 13:
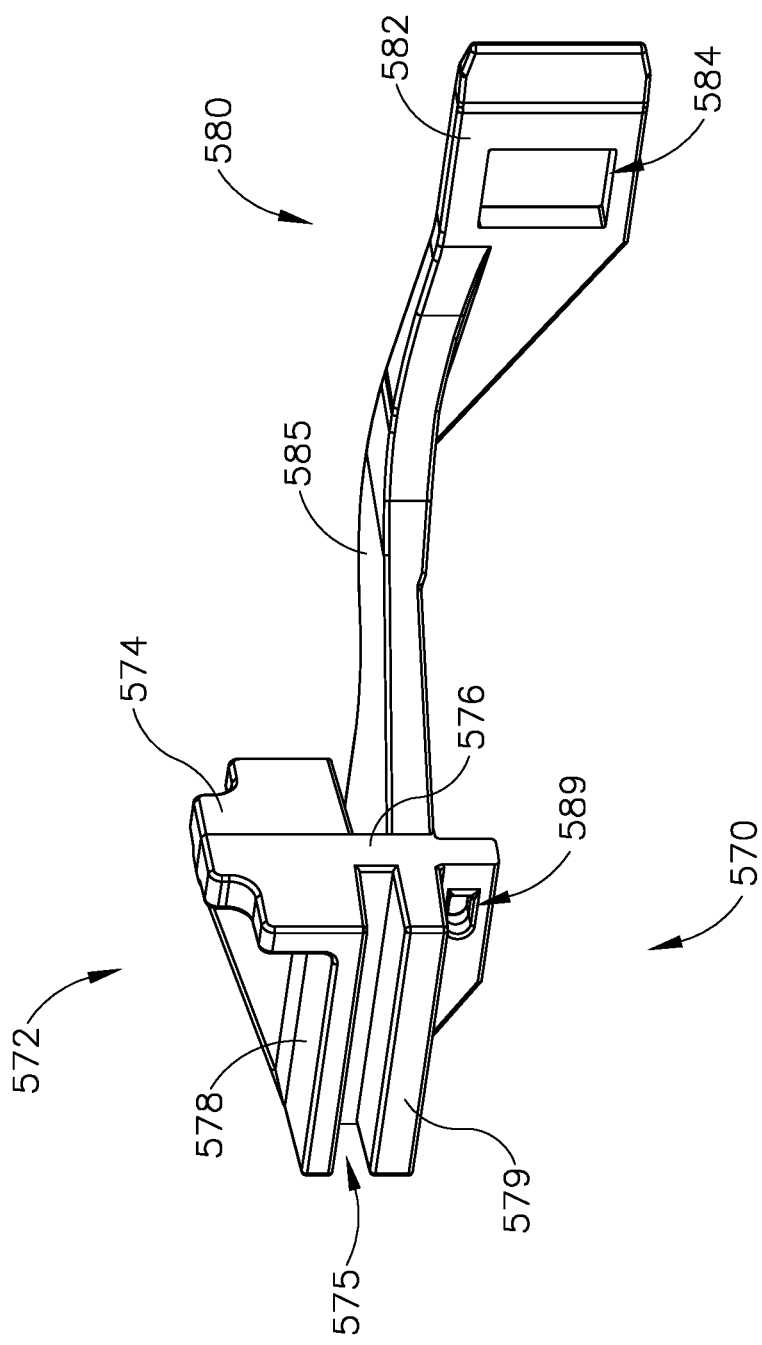
FIG. 13 depicts a perspective view of a translating flag of the carriage assembly of FIG. 9.
Figure 14:
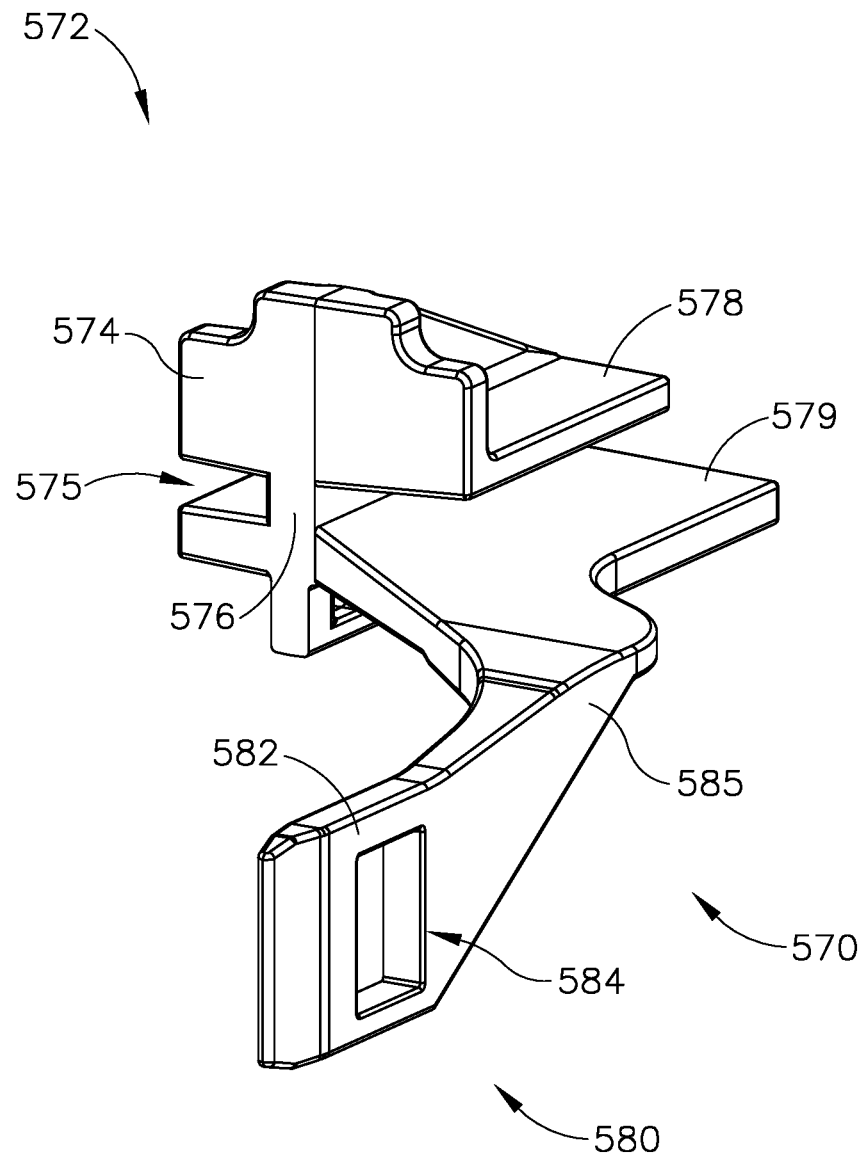
FIG. 14 depicts another perspective view of the translating flag of FIG. 13.

As best seen in FIGS. 13-14, flag portion (580) includes a flag body (582) defining an aperture (584). Laterally offset arm (585) extends from lower lateral projection (579) such that flag portion (580) is laterally aligned with first static flag (560) and second static flag (562). Therefore, as carriage assembly (540) translates due to rotation of lead screw (594), translating flag (570), first static flag (560), and second static flag (562) may translate within U-shaped channel (534) of sensor assembly (530).

C. Exemplary Use of Cartridge Processing Assembly

FIGS. 15A-15D and FIGS. 17A-18D show an exemplary insertion of cartridge (400) into carriage assembly (540). As will be described in greater detail below, sensor assembly (530) and carriage assembly (540) may help verify proper insertion of cartridge (400) into cartridge processing assembly (500); and translate carriage assembly (540) to a home position in preparation to extract sterilant from a properly inserted cartridge (400).

Figure 15A:
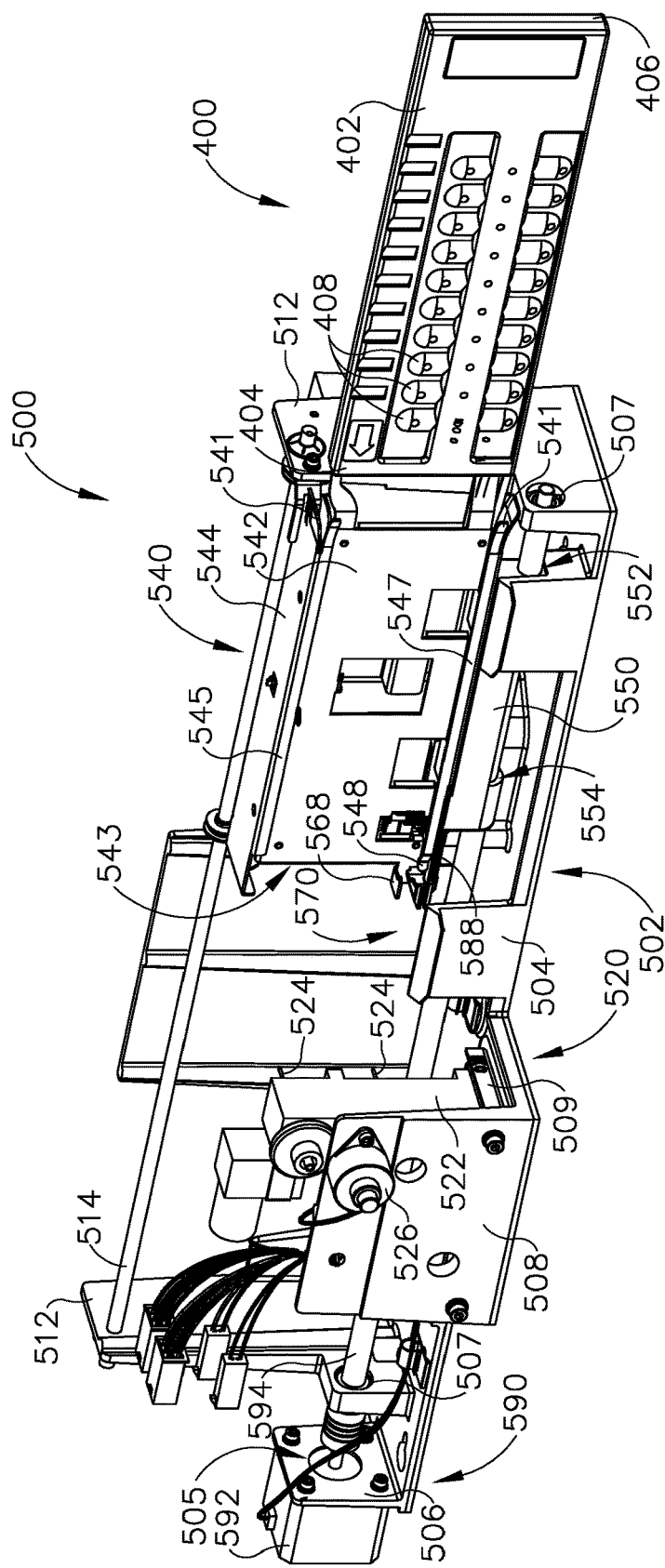
FIG. 15A depicts a perspective view of the cartridge of FIG. 4 aligned with the carriage assembly of FIG. 9 in preparation for insertion of the cartridge into the cartridge processing assembly of FIG. 6.
Figure 17A:
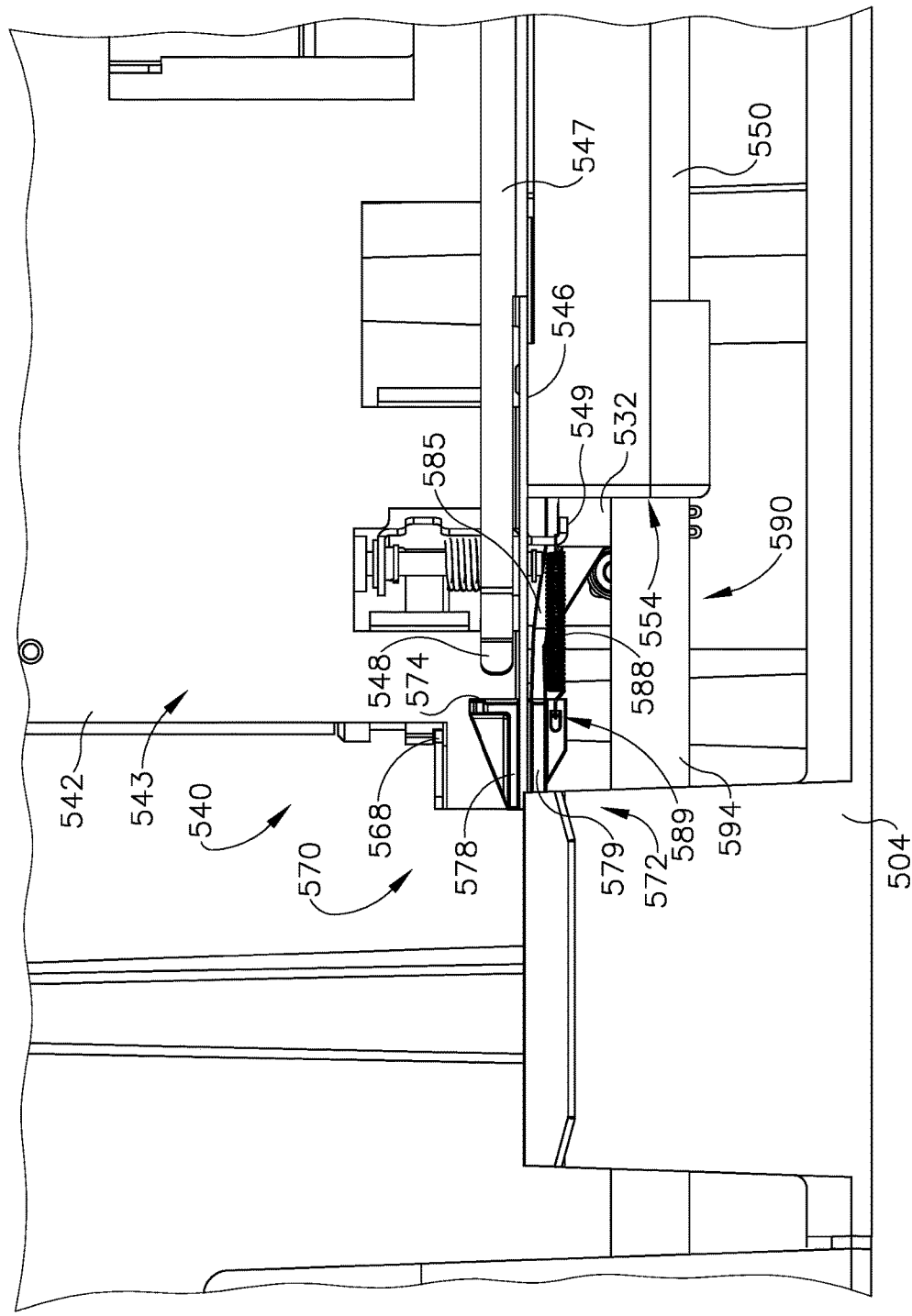
FIG. 17A depicts a side elevational view of the carriage assembly of FIG. 9 in a cartridge receiving position within the cartridge processing assembly of FIG. 6.

First, as shown in FIGS. 15A and 17A, carriage assembly (540) is positioned in a proximal cartridge receiving position within frame assembly (502). An operator may provide user input via touch screen display (160) in order to actuate carriage assembly (540) to the cartridge receiving position. Alternatively, processor (162) may automatically instruct carriage actuation assembly (590) to move carriage assembly (540) to the cartridge receiving position when no cartridge (400) is within carriage assembly (540) or in response to any other suitable condition that would be apparent to one having ordinary skill in the art in view of the teachings herein.

It should be understood that prior to carriage assembly (540) translating to the proximal cartridge receiving position within frame assembly (502) (as shown in FIGS. 15A and 17A), processor (162) may measure the distance between translating flag (570) in the proximal position and first static flag (560). As will be described in greater detail below, this measurement may be used as a datum reference and compared with the distance between first static flag (560) and translating flag (570) in a distal position. This comparison may further be used to determine if cartridge (400) has been properly inserted into carriage assembly (540) within specified tolerances. In some versions, as part of an initialization routine that begins when or shortly after sterilizing cabinet (150) is initially powered on, this datum reference distance may be measured. For instance, as part of this routine, processor (162) may activate motor (592) to drive carriage (540) first to the home position, then to the proximal position where carriage (540) is positioned to receive a new cartridge (400).

It should also be understood that this datum reference calculation routine of carriage (540) being translated first to the home position, then to the proximal position where carriage (540) is positioned to receive a new cartridge (400), may also be performed automatically when sterilant has been extracted from the last pair of reservoir cells (408), when cartridge (400) is deemed expired, when an operator manually initiates the routine, and/or at any other suitable time. Any time this routine is performed, the datum reference may be re-calculated to provide dynamic learning of the datum reference. This may ensure that the datum reference remains as current as possible, which may provide a way to account for physical changes in cabinet (150) that may naturally occur over time. For instance, spring (588) may wear over time, which may result in slight but meaningful changes in the datum reference value. By ensuring that the datum reference updated often, processor (162) may prevent such physical changes from providing false positive or false negative results during the positioning confirmation routines described herein. It should also be understood that the mechanical parts within cabinet (150) will have various tolerances. By providing the dynamic learning of the datum reference as described herein, processor (162) will provide independent compensation for these tolerances. In other words, even before cabinet (150) is used the first time (i.e., such that no parts have become worn or deformed, etc.), different cabinets (150) may provide different datum reference values due simply to mechanical tolerances, and the dynamic learning of the datum reference may account for such tolerances to provide a datum reference that is particularly suited for the particular cabinet (150). Otherwise, if a group of cabinets (150) were to all be prescribed a certain predetermined datum reference value, that particular datum reference value may be inappropriate for one or more cabinets (150) in the group due to slight but meaningful physical differences provided by mechanical tolerances.

As described above, processor (162) is in communication with motor (592) such that processor (162) may track the rotational displacement of rotating motor (592). Rotational displacement of motor (592) may correlate to a change in longitudinal position of carriage assembly (540), which processor (162) may calculate. Additionally, and as mentioned above, optical sensors (536) may be utilized to act as a trigger for processor (162) to initiate actions based on sensors (536) detecting or not detecting objects. Therefore, sensors (536) may instruct processor (162) to count rotational displacement of rotating motor (592) between detection of flag body (582) of translating flag (570) and first static flag (560) as motor (592) actuates carriage assembly (540). Processor (162) may convert the rotational displacement of motor (592) measured between sensors (536) detection of flag body (582) and first static flag (560) into a linear measurement between translating flag (570) and first static flag (560). Now, processor (162) has a datum reference distance between translating flag (570) in the proximal position relative to the rest of carriage assembly (540).

At the point shown in FIGS. 15A and 17A, cartridge (400) is not inserted within carriage assembly (540). As best seen in FIG. 17A, translating flag (570) is in the proximal position due to the force provided by biasing spring (588). It should be understood that contact wall (574) of translating flag (570) is proximal in relation to cartridge stop (568) when translating flag (570) is in the proximal position. It should also be understood that at this point, electric braking may be applied through motor (592) to prevent unintentional rotation of lead screw (594) in response to frictional engagement between complementary threading of lead screw (594) and nut (550).

Figure 15B:
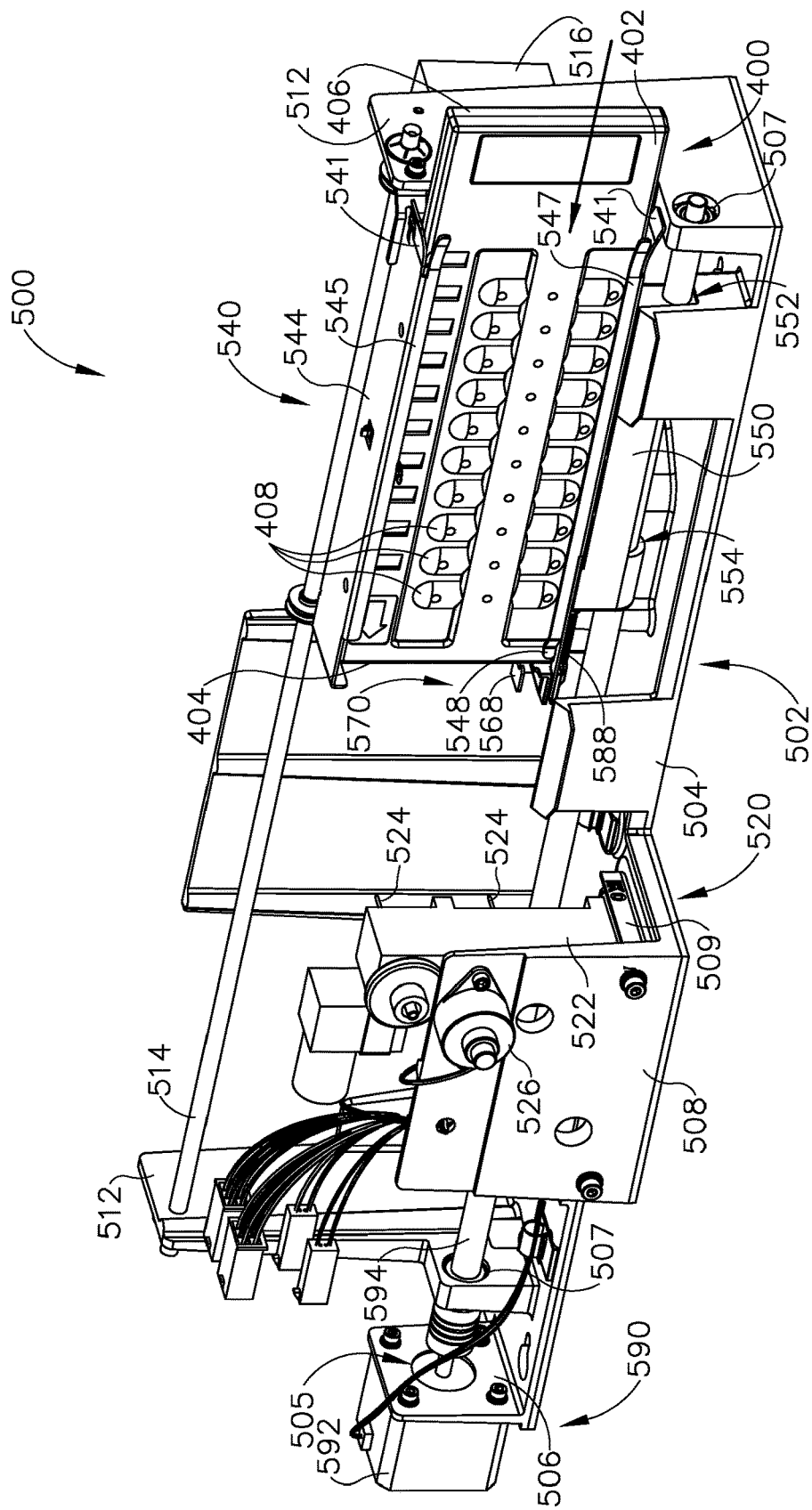
FIG. 15B depicts a perspective view of the cartridge of FIG. 4 partially inserted into the carriage assembly of FIG. 9.
Figure 17B:
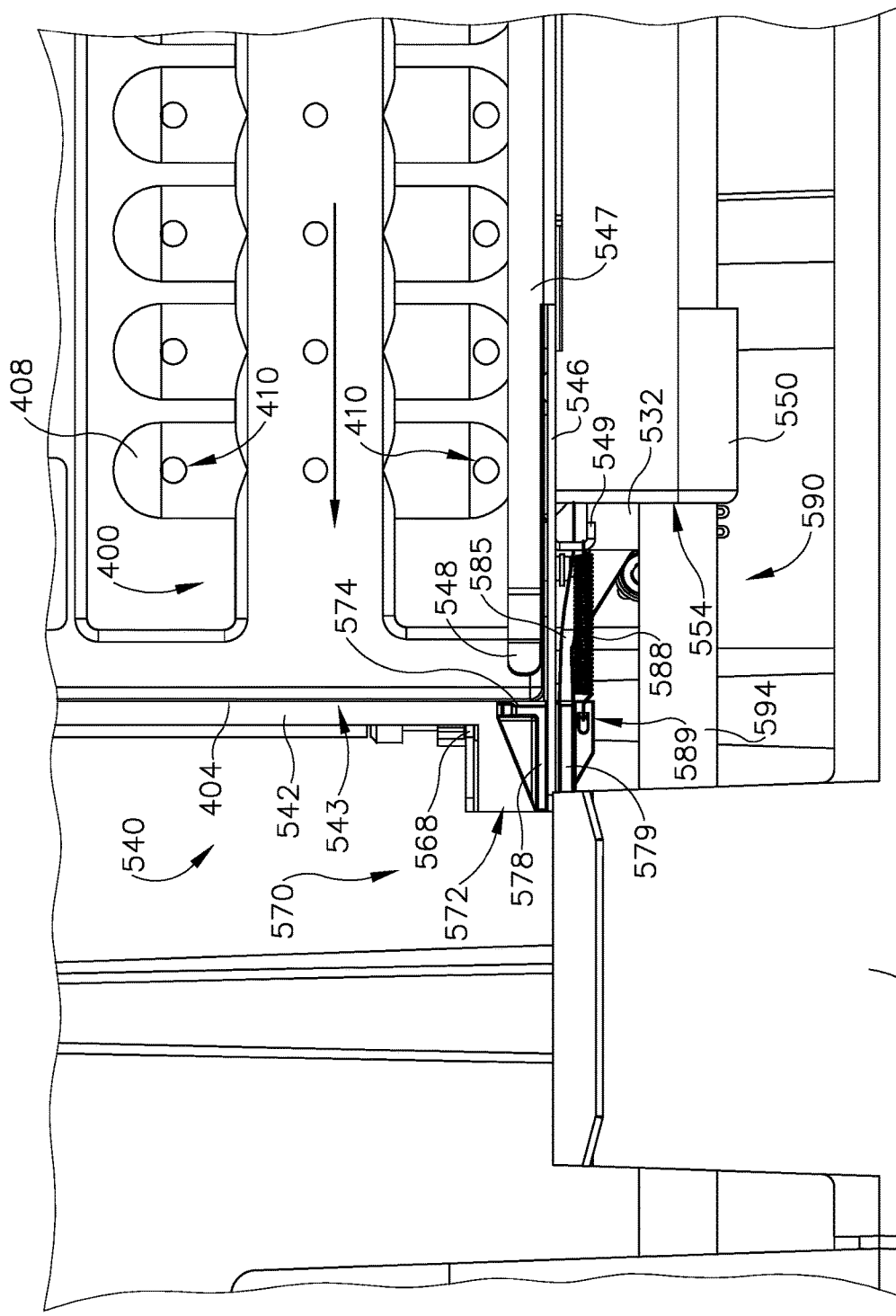
FIG. 17B depicts a side elevational view of the carriage assembly of FIG. 9 in the cartridge receiving position within the cartridge processing assembly of FIG. 6, where the cartridge of FIG. 4 is partially inserted into the carriage assembly.
Figure 18A:
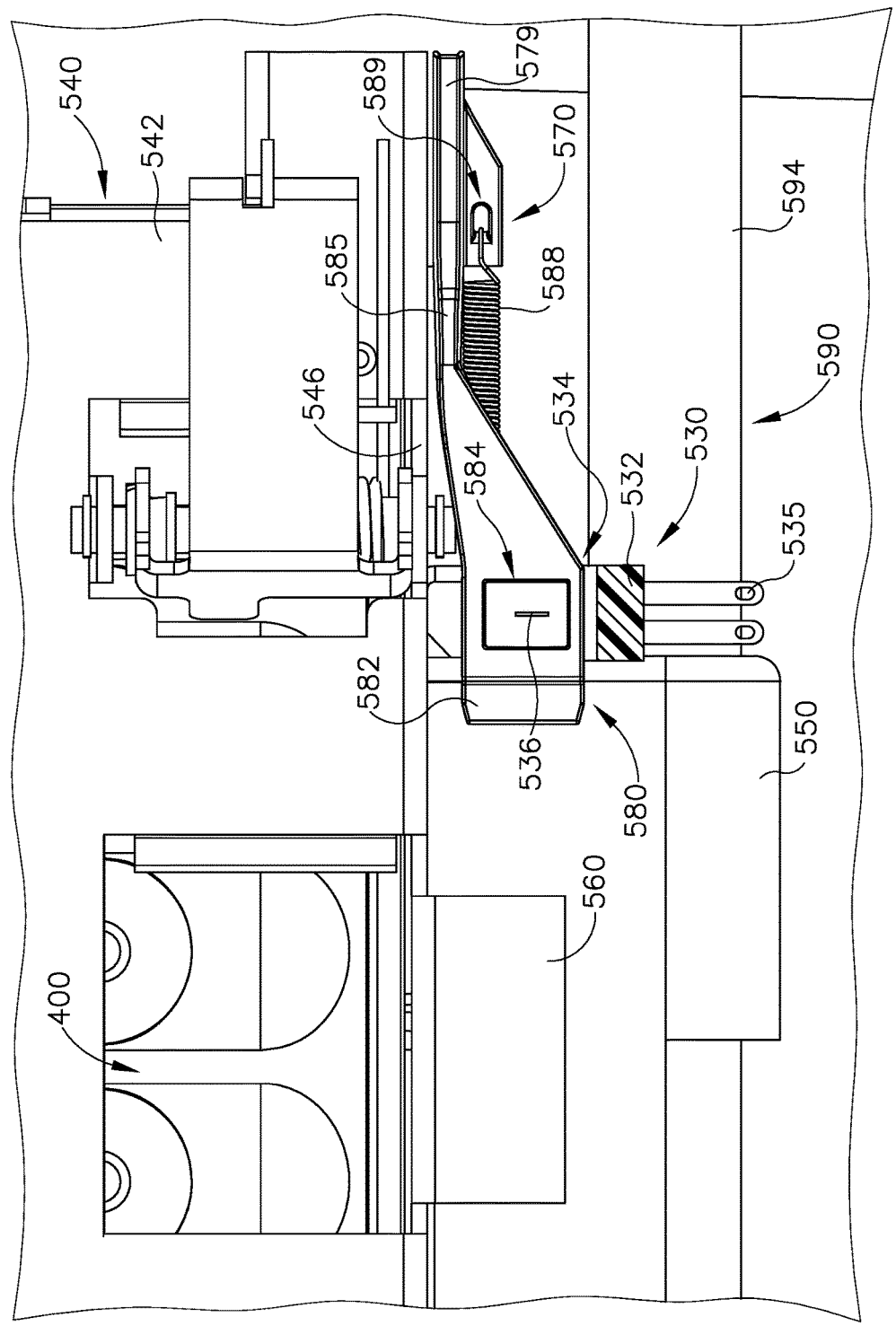
FIG. 18A depicts a cross-sectional view of the carriage assembly of FIG. 9 in the cartridge receiving position within the cartridge processing assembly of FIG. 6, where the cartridge of FIG. 4 is partially inserted into the carriage assembly, taken along line 18-18 of FIG. 8.

Next, as shown in FIGS. 15B, 17B, and 18A, cartridge (400) is inserted into cartridge channel (543) of carriage assembly (540) such that distal end (404) of cartridge (400) is adjacent to contact wall (574). If for some reason, cartridge (400) is improperly inserted within cartridge channel (543) causing unintended longitudinal forces to act upon carriage assembly (540), the electrical brake that is provided through motor (592) will prevent unintended translation of carriage assembly (540) and misalignment of cartridge (400).

It should be understood that, at this point, translating flag (570) is still in the proximal position. Additionally, as best shown in FIG. 18A, flag body (582) of flag portion (580) is located within U-shaped channel (534) of sensor assembly (530). In particular, optical sensors (536) are directly adjacent to aperture (584) such that optical sensors (536) do not detect an object between sensors (536). With optical sensors (536) not detecting a first object between sensors (536), processor (162) has not yet received a signal to activate motor (592) to actuate carriage assembly (540) while measuring rotational displacement of motor (592). As best shown in FIG. 17B, leaf spring (548) of upwardly extending flange (547) is urging cartridge (400) against side panel (542).

Figure 15C:
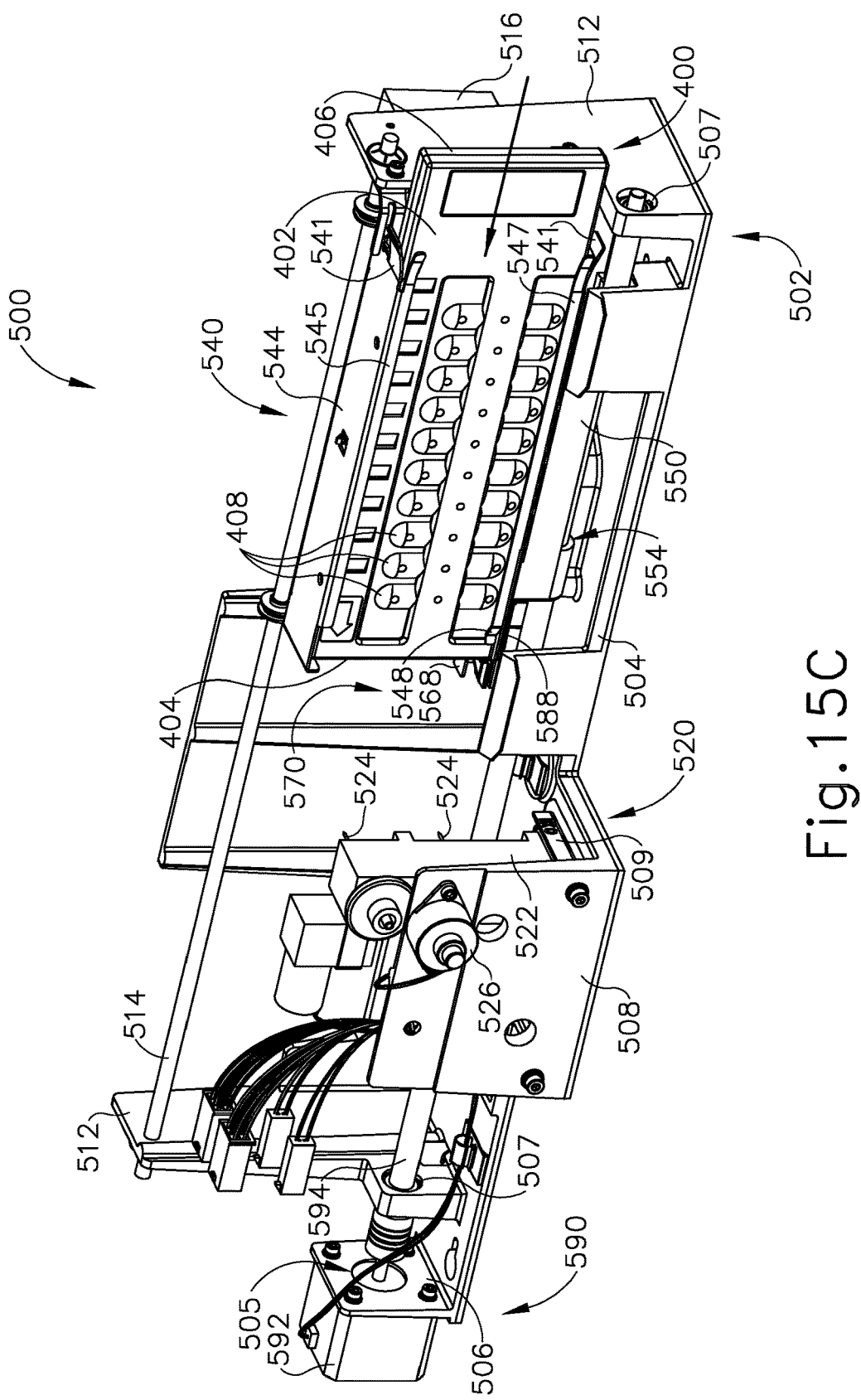
FIG. 15C depicts a perspective view of the cartridge of FIG. 4 further inserted into the carriage assembly of FIG. 9.
Figure 17C:
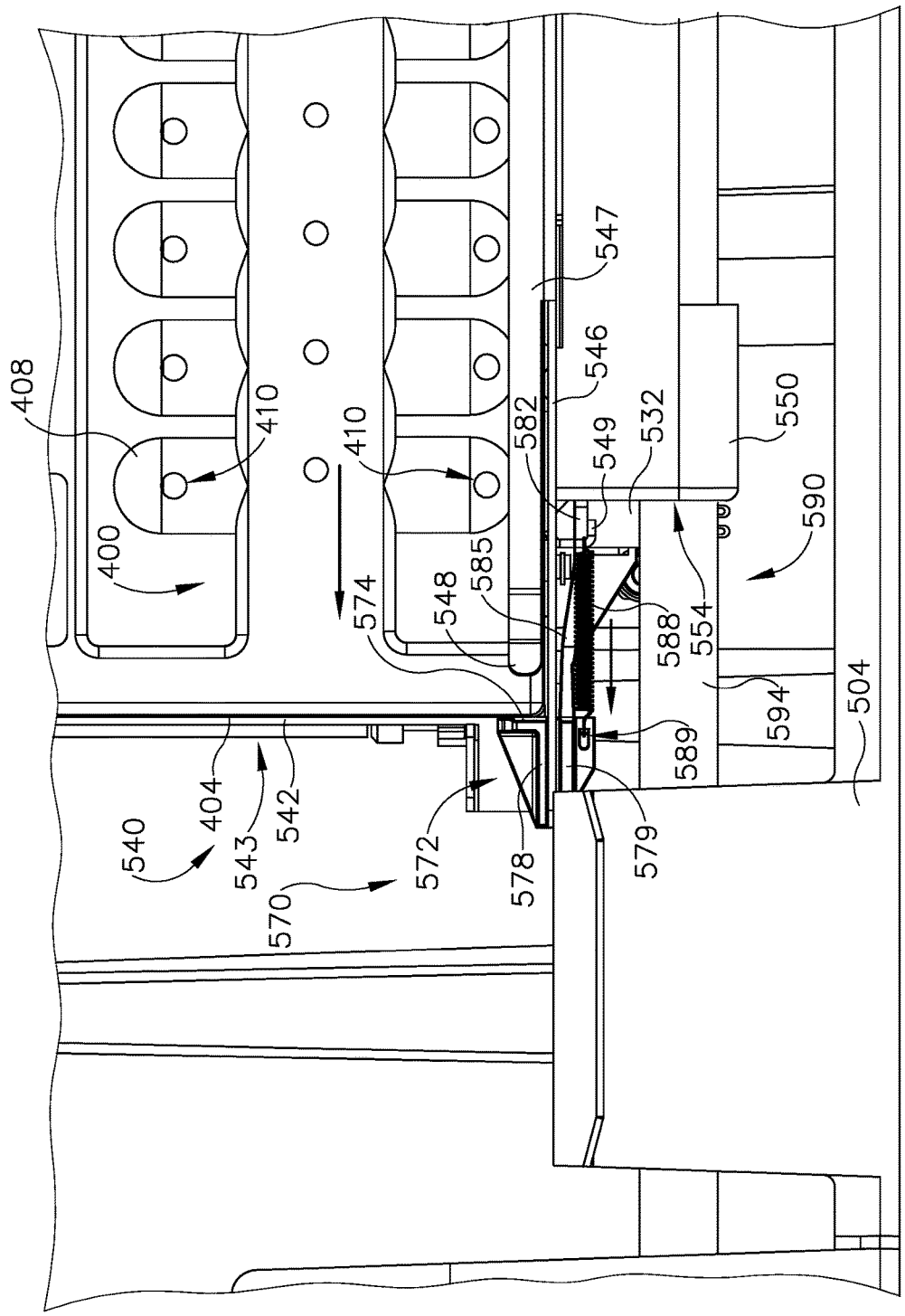
FIG. 17C depicts a side elevational view of the carriage assembly of FIG. 9 in the cartridge receiving position within the cartridge processing assembly of FIG. 6, where the cartridge of FIG. 4 is further inserted into the carriage assembly.
Figure 18B:
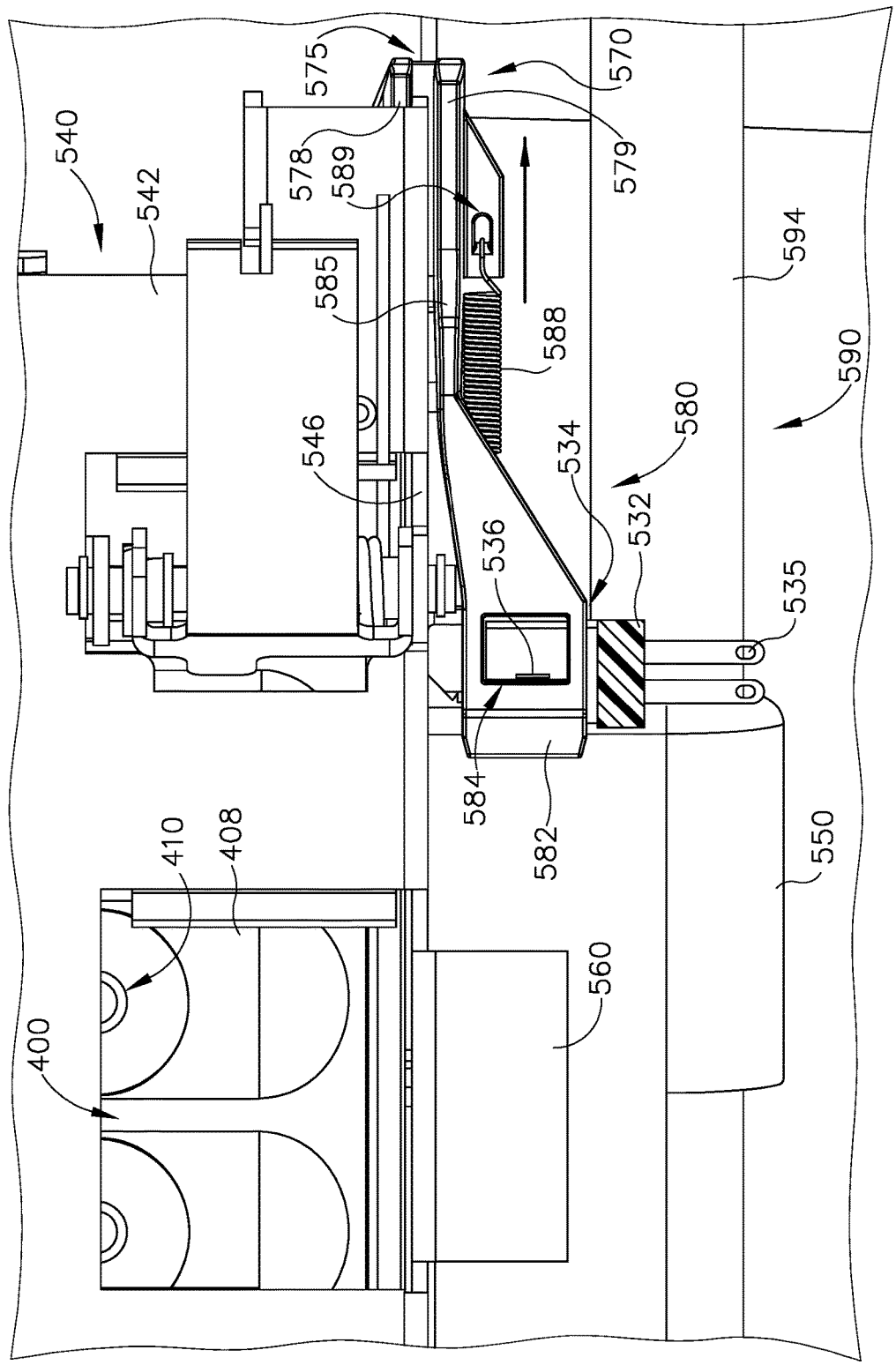
FIG. 18B depicts a cross-sectional view of the carriage assembly of FIG. 9 in the cartridge receiving position within the cartridge processing assembly of FIG. 6, where the cartridge of FIG. 4 is further inserted into the carriage assembly, taken along line 18-18 of FIG. 8.

Next, as shown in FIGS. 15C, 17C, and 18B, cartridge (400) is further inserted into cartridge channel (543) of carriage assembly (540) such that distal end (404) of cartridge (400) bears against contact wall (574) to move translating flag (570) to a distal position. While translating flag (570) is pushed to the distal position, bias spring (588) imparts a proximally oriented force on cartridge (400) via contact wall (574). However, the frictional force provided by leaf spring (548) imparted on cartridge (400) is strong enough to overcome the bias force of spring (588) and keep translation flag (570) in the distal position. At this point, flag body (582) of flag portion (580) is still located within U-shaped channel (534). However, optical sensors (536) are now directly adjacent to flag body (582) instead of aperture (584). Therefore, optical sensors (536) detect an object between sensors (536).

Figure 15D:
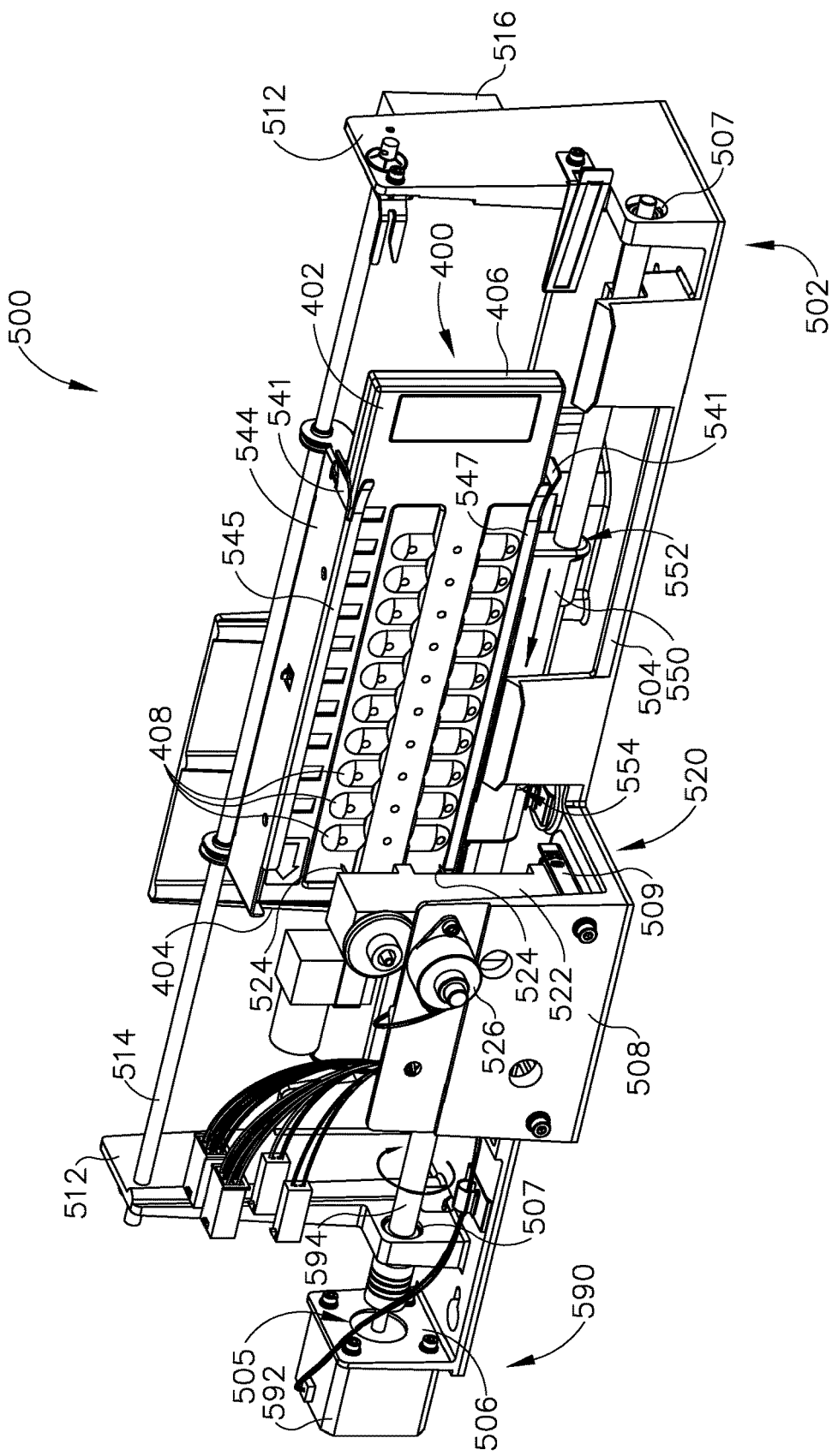
FIG. 15D depicts a perspective view of the cartridge of FIG. 4 and the carriage assembly of FIG. 9 unitarily translating within the cartridge processing assembly of FIG. 6.
Figure 17D:
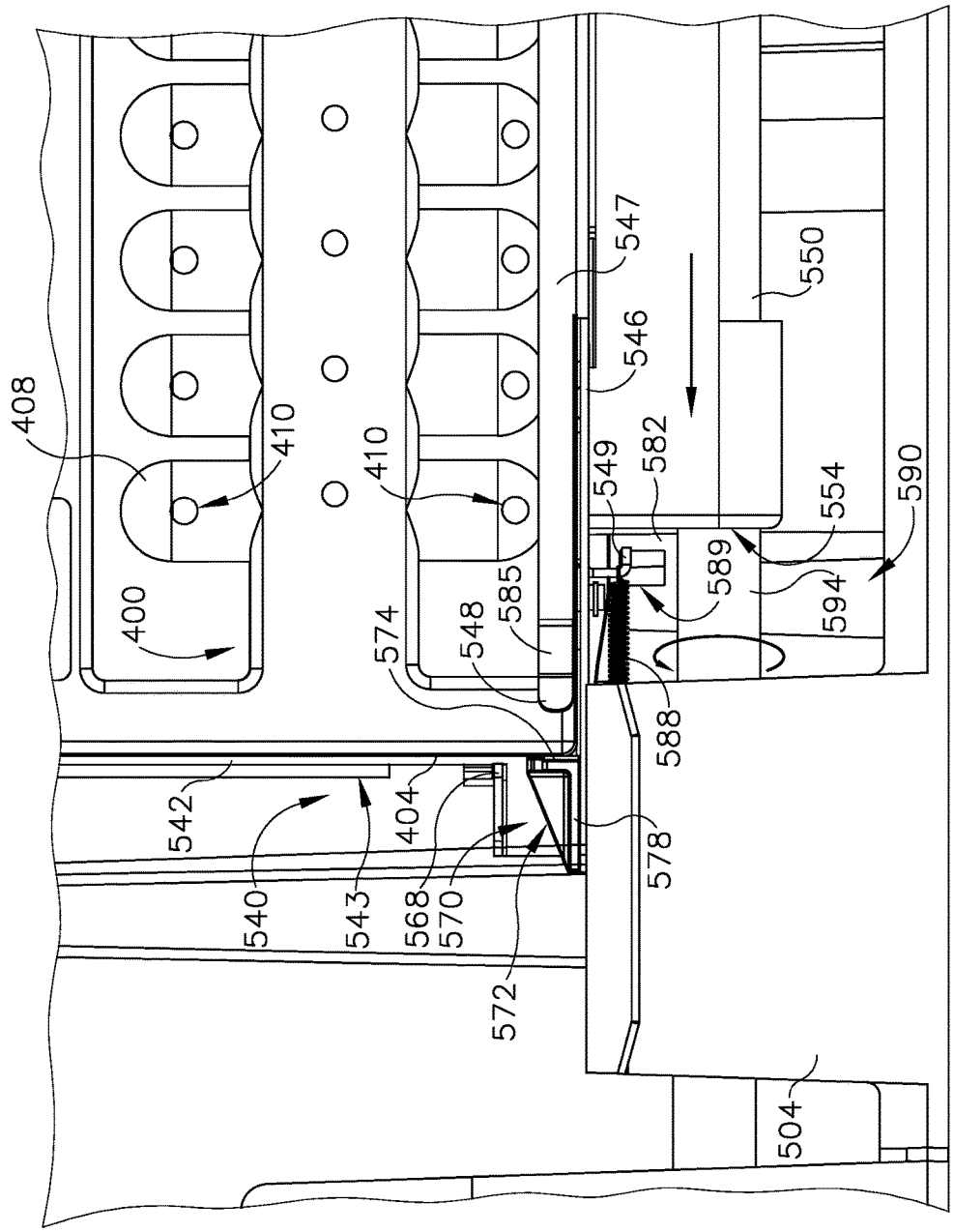
FIG. 17D depicts a side elevational view of the carriage assembly of FIG. 9 and the cartridge of FIG. 4 actuated distally within the carriage processing assembly of FIG. 6.
Figure 18C:
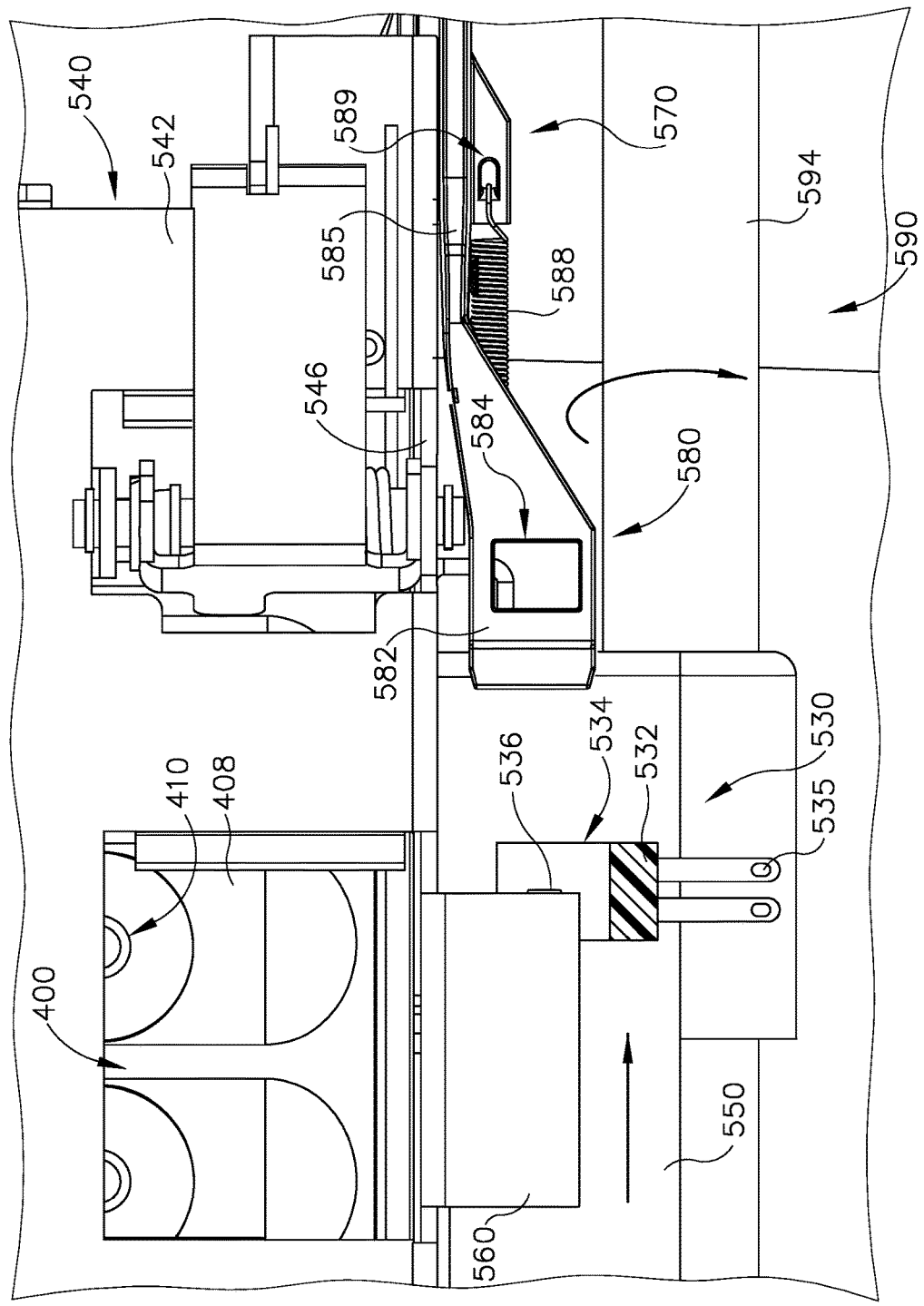
FIG. 18C depicts a cross-sectional view of the carriage assembly of FIG. 9 and the cartridge of FIG. 4 actuated distally within the carriage processing assembly of FIG. 6, taken along line 18-18 of FIG. 8.
Figure 18D:
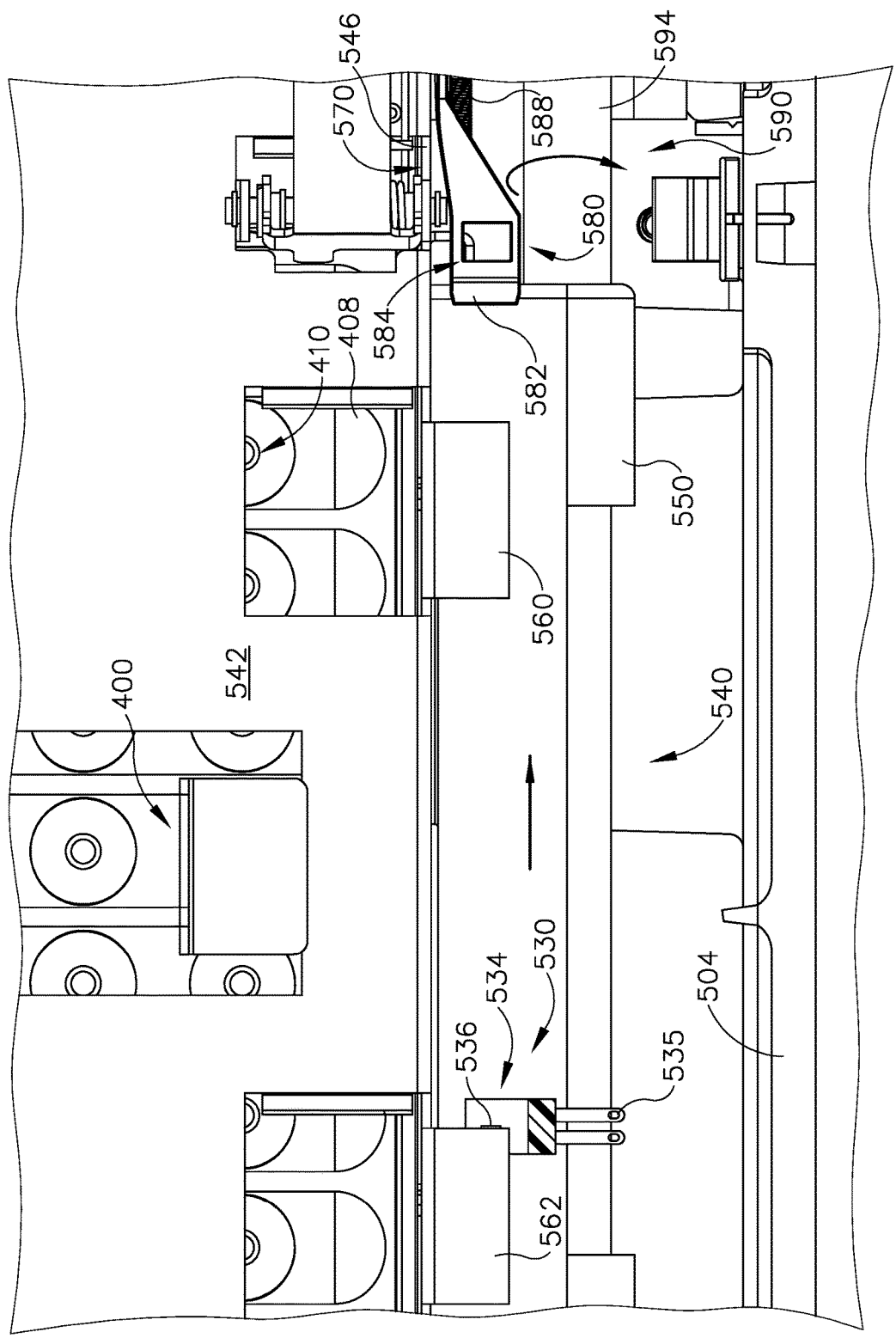
FIG. 18D depicts a cross-sectional view of the carriage assembly of FIG. 9 and the cartridge of FIG. 4 actuated further distally within the carriage processing assembly of FIG. 6, taken along line 18-18 of FIG. 8.

Once optical sensors (536) detect flag body (582), optical sensors (536) may send signals to processor (162). Optical sensors (536) may send an initial signal to processor (162) to debounce further sensor signals for a predetermined amount to time, such as 100 ms. This debouncing time may allow for further insertion of cartridge (400) within carriage assembly (540), although this is merely optional. Optical sensors (536) may then signal to processor (162) to activate motor (592) to translate carriage assembly (540) distally within frame assembly (502). Additionally, optical sensors (536) may also signal to processor (162) to begin counting the rotations of motor (592) until optical sensors (536) detect first static flag (560) as shown in FIGS. 15D, 17D, and 18C.

When optical sensors (536) detect first static flag (560), sensors (536) may signal to processor (162) to compare the number of motor (592) rotations counted at that point to an expected number of motor (592) rotations. In other words, processor (162) may determine whether motor (592) has rotated an expected number of times during the range of travel associated with flag body (582) first triggering sensors (536) followed by first static flag (560) triggering sensors (536). If the number of actual rotations matches the expected number of rotations, then processor (162) determines that cartridge (400) was properly inserted into carriage assembly (540); and processor (162) may continue activation of motor (592) to continue driving carriage assembly (540) and cartridge (400) distally.

It should be understood that the number of rotations of motor (592) during the time between sensor (536) detection of flag body (582) and sensor detection of first static flag (560) will correlate with the linear distance between flag body (582) and first static flag (560). It should also be understood that the linear distance between flag body (582) and first static flag (560) may vary based on the extent to which translating flag (570) has translated distally relative to the rest of carriage assembly (540). Moreover, the extent to which translating flag (570) has translated distally relative to the rest of carriage assembly (540) will vary based on whether cartridge (400) has been properly inserted into carriage assembly (540). Thus, if cartridge (400) has been properly inserted into carriage assembly (540), the linear distance between flag body (582) and first static flag (560) will be appropriate, which will result in motor (592) rotating an expected number of times during the time between sensor (536) detection of flag body (582) and sensor detection of first static flag (560). However, if cartridge (400) has not been properly inserted into carriage assembly (540), the linear distance between flag body (582) and first static flag (560) will not be appropriate (e.g., the distance will be too short), which will result in motor (592) rotating an inappropriate number of times (e.g., too few number of times) during the time between sensor (536) detection of flag body (582) and sensor detection of first static flag (560). Thus, in the event that processor (162) determines that motor (592) has failed to rotate the expected number of times during the range of travel associated with flag body (582) first triggering sensors (536) followed by first static flag (560) triggering sensors (536), processor (162) may trigger an error routine. For instance, processor (162) may activate motor (592) to rotate in reverse, thereby driving cartridge (400) and carriage assembly (540) proximally to re-present cartridge (400) to the operator; and/or present a message via touch screen display (160) indicating that cartridge (400) was inserted improperly. The operator may thereby be prompted to remove and re-insert cartridge (400) properly.

Assuming the case where processor (162) determines that cartridge (400) was properly inserted into carriage assembly (540) based on the motor (592) rotations tallying up to the expected value as described above, processor (162) will continue activation of motor (592) to continue driving carriage assembly (540) and cartridge (400) distally. During this range of continued travel, information area (412) may eventually pass before ID reader sensor (518), triggering automated reading of the label, tag, etc., that is located on information area (412). Processor (162) may process data obtained through this reading and thereby determine whether use of cartridge (400) would be appropriate. For instance, processor (162) may determine whether cartridge (400) contains a sterilant that is consistent with a sterilization cycle selected by the operator, whether cartridge (400) is authentic (e.g., originating from a trusted source), whether cartridge (400) has been used before, etc. Various suitable ways in which processor (162) may determine whether use of cartridge (400) would be appropriate will be apparent to those of ordinary skill in the art in view of the teachings herein.

In the event that processor (162) determines that use of cartridge (400) would be appropriate based on the reading by ID reader sensor (518), processor (162) may continue activating motor (592), thereby resulting in continued distal travel of carriage assembly (540) and cartridge (400). In the event that processor (162) determines that use of cartridge (400) would not be appropriate based on the reading by ID reader sensor (518), processor (162) may execute an error routine. For instance, processor (162) may activate motor (592) to rotate in reverse, thereby driving cartridge (400) and carriage assembly (540) proximally to re-present cartridge (400) to the operator; and/or present a message via touch screen display (160) indicating that cartridge (400) is unusable. The operator may thereby be prompted to remove cartridge (400) and replace cartridge (400) with an appropriate cartridge (400).

Assuming the case where processor (162) determines that use of cartridge (400) is appropriate based on the reading by ID reader sensor (518), processor (162) will continue activation of motor (592) to continue driving carriage assembly (540) and cartridge (400) distally. Carriage assembly (540) eventually reaches the position shown in FIG. 18D, where second static flag (562) is between sensors (536). When sensors (536) detect second static flag (562), processor (162) may stop motor (592). At this stage, cartridge (400) and carriage assembly (540) are the home position in preparation for the extraction process shown in FIGS. 16A-16B.

After extraction assembly (520) extracts sterilant from the first (distal-most) pair of reservoir cells (408), and processor (162) is then instructed to execute another sterilization cycle, processor (162) may activate motor (592) once again to drive carriage assembly (540) and cartridge (400) distally to index the next pair of reservoir cells (408) with extraction assembly (520). In order to provide proper positioning of the next pair of reservoir cells (408), to thereby properly index the next pair of reservoir cells (408) with extraction assembly (520), processor (162) may simply track the number of rotations of motor (592) and stop motor (592) once the number of rotations reaches a predetermined value that is associated with carriage assembly (540) and cartridge (400) traveling the appropriate distance. This sequence may be repeated for subsequent sterilization cycles until sterilant has been extracted from the last (proximal-most) reservoir cells (408). When this occurs, sterilizing cabinet (150) may dispose of the spent cartridge (400) in any suitable fashion and prompt the operator to insert a new cartridge (400).

In addition to the foregoing, the cartridge (400) handling features of sterilizing cabinet (150) (and/or other features of sterilizing cabinet (150)) may be configured and operable in accordance with at least some of the teachings of U.S. Pat. No. 8,440,139, entitled "Method of Delivering Liquid Sterilant to a Sterilizer," issued May 14, 2013, the disclosure of which is incorporated by reference herein. Various suitable ways in which the teachings herein may be combined with the teachings of U.S. Pat. No. 8,440,139 will be apparent to those of ordinary skill in the art.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A sterilization system comprising: (a) a sterilization chamber configured to receive and sterilize at least one medical device; (b) a processor; and (c) a sterilization module comprising: (i) a frame assembly comprising a sensor in communication with the processor, (ii) an extraction assembly in fluid communication with the sterilization chamber, wherein the extraction assembly is configured to extract a sterilant fluid from a cartridge and transfer the sterilant fluid to the sterilization chamber, and (iii) a carriage assembly comprising: (A) a motor in communication with the processor, (B) a carriage body coupled with the motor, wherein the carriage body is configured to receive the cartridge, and (C) a translating flag configured to move from a first position to a second position relative to the carriage body in response to the carriage body receiving the cartridge, wherein the sensor is configured to detect movement of the translating flag from the first position to the second position.

Example 2

The sterilization system of Example 1, wherein the motor is configured to drive the carriage body distally in response to the sensor detecting the movement of the translating flag from the first position to the second position.

Example 3

The sterilization system of Example 2, wherein the carriage body comprises a first static flag, wherein the sensor is configured to detect the first static flag, wherein the motor is configured to drive the carriage body distally in response to the sensor detecting the translating flag actuating form the first position to the second position until the sensor detects the first static flag.

Example 4

The sterilization system of Example 3, wherein the processor is configured to calculate a first distance between the translating flag in the first position and the static flag, wherein the processor is configured to store a datum distance based in part on the first distance.

Example 5

The sterilization system of Example 4, wherein the processor is configured to calculate a second distance between the translating flag in the second position and the first static flag.

Example 6

The sterilization system of Example 5, wherein the motor is configured to proximally actuate the carriage body and thereby reject the cartridge if the second distance is less than the datum distance.

Example 7

The sterilization system of Example 6, wherein the carriage body further comprises a second static flag, wherein the sensor is configured to detect the second static flag, wherein the motor is configured to distally actuate the carriage body toward the second static flag if the second distance is greater than or equal to the datum distance.

Example 8

The sterilization system of Example 7, wherein the motor is configured to stop actuating the carriage body in response to the sensor detecting the second static flag.

Example 9

The sterilization system of any one or more of Examples 1 through 8, wherein the translating flag is resiliently biased toward the first position.

Example 10

The sterilization system of any one or more of Examples 1 through 9, wherein the translating flag comprises a contact wall configured to interface with the cartridge.

Example 11

The sterilization system of any one or more of Examples 1 through 10, wherein the carriage assembly further comprises a resilient member configured to urge the cartridge against the carriage body.

Example 12

The sterilization system of any one or more of Examples 1 through 11, wherein the translating flag defines an aperture, wherein the sensor is positioned to be adjacent to the aperture when the translating flag is in the first position.

Example 13

The sterilization system of any one or more of Examples 1 through 12, wherein the frame comprises a sensor body defining a U-shaped channel, wherein the sensor is located within the U-shaped channel.

Example 14

The sterilization system of any one or more of Examples 1 through 13, wherein the carriage assembly further comprises a lead screw extending from the motor, wherein the lead screw associated with the carriage body, wherein the motor is configured to rotate the lead screw such that the lead screw is thereby operable to translate the carriage body.

Example 15

The sterilization system of any one or more of Examples 1 through 14, wherein the motor comprises a stepper motor.

Example 16

The sterilization system of any one or more of Examples 1 through 15, wherein the processor is configured to provide electric braking through the motor.

Example 17

A sterilization system comprising: (a) a sterilization chamber configured to receive and sterilize at least one medical device; (b) a processor; and (c) a sterilization module in fluid communication with the sterilization chamber and in electrical communication with the processor, wherein the sterilization module comprises: (i) a frame assembly comprising a sensor in communication with the processor, (ii) an extraction assembly in fluid communication with the sterilization chamber and in electrical communication with the processor, wherein the extraction assembly is configured to extract a sterilant fluid from a cartridge and transfer the sterilant fluid to the sterilization chamber, and (iii) a carriage assembly configured to actuate relative to the frame assembly, wherein the carriage assembly comprises: (A) a carriage defining a cartridge channel configured to receive the cartridge, (B) a translating flag configured to move from a first position to a second position relative to the carriage in response to the carriage assembly receiving the cartridge, wherein the sensor is configured to detect movement of the translating flag from the first position to the second position, and (C) a static flag fixed to the carriage, wherein the sensor is configured to detect the static flag, wherein the processor is configured to measure a first distance between the static flag and the translating flag in the first position, wherein the processor is configured to measure a second distance between the static flag and the translating flag in the second position, wherein the processor is configured to compare the first distance and the second distance to determine if the cartridge is properly inserted within the carriage assembly.

Example 18

The sterilization system of Example 17, wherein the translating flag is resiliently biased to the first position.

Example 19

A sterilization system comprising: (a) a sterilization chamber configured to receive and sterilize at least one medical device; (b) a processor; and (c) a sterilization module in fluid communication with the sterilization chamber and in electrical communication with the processor, wherein the sterilization module comprises: (i) a frame assembly comprising a sensor in communication with the processor, (ii) an extraction assembly in fluid communication with the sterilization chamber and in electrical communication with the processor, wherein the extraction assembly is configured to extract a sterilant fluid from a cartridge and transfer the sterilant fluid to the sterilization chamber, (iii) a carriage assembly defining a cartridge channel configured to receive a cartridge, wherein the carriage assembly comprises: (A) a carriage defining a cartridge channel configured to receive the cartridge, and (B) a translating flag configured to move from a first position to a second position relative to the carriage in response to the carriage assembly receiving the cartridge, wherein the sensor is configured to detect movement of the translating flag from the first position to the second position, and (iv) a motor configured to actuate the carriage assembly in response to movement of the translating flag from the first position to the second position.

Example 20

The sterilization system of Example 19, further comprising a cartridge configured to fit in the carriage, wherein the cartridge contains a liquid sterilant.

VI. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A sterilization system comprising:
    (a) a sterilization chamber configured to receive and sterilize at least one medical device;
    (b) a processor; and
    (c) a sterilization module comprising:
        (i) a frame assembly comprising a sensor in communication with the processor,
        (ii) an extraction assembly in fluid communication with the sterilization chamber, wherein the extraction assembly is configured to extract a sterilant fluid from a cartridge and transfer the sterilant fluid to the sterilization chamber, and
        (iii) a carriage assembly comprising:
            (A) a motor in communication with the processor,
            (B) a carriage body coupled with the motor, wherein the motor is configured to drive the carriage body relative to the frame assembly, wherein the carriage body is configured to receive the cartridge, and
            (C) a translating flag configured to move from a first position to a second position relative to the carriage body in response to the carriage body receiving the cartridge, wherein the sensor is configured to detect movement of the translating flag from the first position to the second position, wherein the translating flag is configured to remain in the second position relative to the carriage body when the motor drives the carriage body after the carriage body suitably received the cartridge.

2. The sterilization system of claim 1, wherein the motor is configured to drive the carriage body distally in response to the sensor detecting the movement of the translating flag from the first position to the second position.

3. The sterilization system of claim 2, wherein the carriage body comprises a first static flag, wherein the sensor is configured to detect the first static flag, wherein the motor is configured to drive the carriage body distally in response to the sensor detecting the translating flag actuating form the first position to the second position until the sensor detects the first static flag.

4. The sterilization system of claim 3, wherein the processor is configured to calculate a first distance between the translating flag in the first position and the static flag, wherein the processor is configured to store a datum distance based in part on the first distance.

5. The sterilization system of claim 4, wherein the processor is configured to calculate a second distance between the translating flag in the second position and the first static flag.

6. The sterilization system of claim 5, wherein the motor is configured to proximally actuate the carriage body and thereby reject the cartridge if the second distance is less than the datum distance.

7. The sterilization system of claim 6, wherein the carriage body further comprises a second static flag, wherein the sensor is configured to detect the second static flag, wherein the motor is configured to distally actuate the carriage body toward the second static flag if the second distance is greater than or equal to the datum distance.

8. The sterilization system of claim 7, wherein the motor is configured to stop actuating the carriage body in response to the sensor detecting the second static flag.

9. The sterilization system of claim 1, wherein the translating flag is resiliently biased toward the first position.

10. The sterilization system of claim 1, wherein the translating flag comprises a contact wall configured to interface with the cartridge.

11. The sterilization system of claim 1, wherein the carriage assembly further comprises a resilient member configured to urge the cartridge against the carriage body.

12. The sterilization system of claim 1, wherein the translating flag defines an aperture, wherein the sensor is positioned to be adjacent to the aperture when the translating flag is in the first position.

13. The sterilization system of claim 1, wherein the frame comprises a sensor body defining a U-shaped channel, wherein the sensor is located within the U-shaped channel.

14. The sterilization system of claim 1, wherein the carriage assembly further comprises a lead screw extending from the motor, wherein the lead screw associated with the carriage body, wherein the motor is configured to rotate the lead screw such that the lead screw is thereby operable to translate the carriage body.

15. The sterilization system of claim 1, wherein the motor comprises a stepper motor.

16. The sterilization system of claim 1, wherein the processor is configured to provide electric braking through the motor.

17. A sterilization system comprising:
(a) a sterilization chamber configured to receive and sterilize at least one medical device;
(b) a processor; and
(c) a sterilization module comprising:
  (i) a frame assembly comprising a sensor in communication with the processor,
  (ii) an extraction assembly in fluid communication with the sterilization chamber, wherein the extraction assembly is configured to extract a sterilant fluid from a cartridge and transfer the sterilant fluid to the sterilization chamber, and
  (iii) a carriage assembly comprising:
    (A) a motor in communication with the processor,
    (B) a carriage body coupled with both the motor and the frame assembly, wherein the carriage body is configured to receive the cartridge, wherein the motor is configured to drive the carriage body relative to the frame assembly, and
    (C) a translating flag configured to move from a first position to a second position relative to the carriage body in response to the carriage body receiving the cartridge, wherein the sensor is configured to detect movement of the translating flag from the first position to the second position.

18. The sterilization system of claim 17, wherein the translating flag is biased toward the a first position.

19. A sterilization system comprising:
(a) a sterilization chamber configured to receive and sterilize at least one medical device;
(b) a processor; and
(c) a sterilization module comprising:
  (i) a frame assembly comprising a sensor in communication with the processor,
  (ii) an extraction assembly in fluid communication with the sterilization chamber, wherein the extraction assembly is configured to extract a sterilant fluid from a cartridge and transfer the sterilant fluid to the sterilization chamber, and
  (iii) a carriage assembly comprising:
    (A) a motor in communication with the processor,
    (B) a carriage body coupled with the motor, wherein the carriage body is configured to receive the cartridge, and
    (C) a translating flag configured to move from a first position to a second position relative to the carriage body in response to the carriage body receiving the cartridge, wherein the sensor is configured to detect movement of the translating flag from the first position to the second position, and
    (D) a spring connected to the translating flag and the carriage body, wherein the spring biases the translating flag to the first position.

20. The sterilization system of claim 19, wherein the translating flag is slidably coupled to the carriage body.

* * * * *